United States Patent
Karatzas et al.

(10) Patent No.: US 6,713,662 B1
(45) Date of Patent: *Mar. 30, 2004

(54) PRODUCTION OF COLLAGEN IN THE MILK OF TRANSGENIC MAMMALS

(75) Inventors: Costas N. Karatzas, Beaconsfield (CA); Frank Pieper, Utrecht (NL); Ineke De Wit, Leiden (NL); Richard Berg, Los Altos, CA (US); Gerard Platenburg, Voorschoten (NL); Paul David Toman, Mountain View, CA (US)

(73) Assignees: Pharming Intellectual Property B.V., Leiden (NL); Cohesion Technologies, Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 454 days.

(21) Appl. No.: 08/482,173

(22) Filed: Jun. 7, 1995

Related U.S. Application Data

(63) Continuation-in-part of application No. 08/281,493, filed on Jul. 27, 1994, now abandoned.

(51) Int. Cl.$^7$ .......................... C12P 21/00; A01K 67/00; C12N 15/00

(52) U.S. Cl. ................ 800/14; 800/7; 800/15; 800/18; 435/325; 426/580; 426/587; 426/588

(58) Field of Search .................... 800/2, DIG. 1–4, 800/7, 14, 25, 15, 18; 435/172.3, 325; 536/23.1, 23.5; 119/DIG. 1; 20/23; 424/157.1, 535; 531/580; 426/580, 587, 588

(56) References Cited

U.S. PATENT DOCUMENTS

| 5,667,839 A | | 9/1997 | Berg | 426/657 |
| 5,895,833 A | * | 4/1999 | Berg | 800/14 |
| 5,962,648 A | * | 10/1999 | Berg | 530/356 |

OTHER PUBLICATIONS

Houdebine, L. M. Production of pharmaceutical proteins from transgenic animals. J. of Biotech., vol. 34, pp. 269–287, 1994.*

* cited by examiner

*Primary Examiner*—Deborah Crouch
(74) *Attorney, Agent, or Firm*—Townsend and Townsend and Crew LLP

(57) ABSTRACT

The invention provides transgenic nonhuman mammals capable secreting exogenous procollagen or collagen into their milk. The mammals are healthy and capable of producing procollagen or collagen at high levels, usually in trimeric form. Suitable transgenes for incorporation into the mammals are also provided.

26 Claims, 16 Drawing Sheets

D. Partial map of p(8kb, CS)

E. Partial map of pWE15ΔCΔS

B.

28S--

28S--

A.

B.

1 2  3 4 5 6 7 8 9 10 11 12 13 14 15 16 17

—28S

— 18S

PRODUCTION OF COLLAGEN IN THE MILK OF TRANSGENIC MAMMALS

CROSS-REFERENCE TO RELATED APPLICATION

This application is a continuation-in-part of U.S. Ser. No. 08/281,493 filed Jul. 27, 1994, abandoned, which is incorporated by reference in its entirety for all purposes.

TECHNICAL FIELD

The invention relates generally to transgenic nonhuman mammals producing procollagen or collagen in their milk.

BACKGROUND

Collagen is a family of fibrous proteins present in all multicellular organisms. Collagen forms insoluble fibers having a high tensile strength. Collagen is the major fibrous element of skin, bone tendon cartilage, blood vessels and teeth. It is present in nearly all organs and serves to hold cells together in discrete units. Recently, collagen has assumed a therapeutic importance in reconstructive and cosmetic surgical procedures.

The process by which collagen is expressed, processed and ultimately assembled into mature collagen fibers is complex. At least 28 distinct collagen genes have been reported, whose expression products combine to form at least 14 different forms of collagen. Different forms of collagen are associated with different tissue types. For example, type I collagen is distributed predominantly in skin, tendon, bone and cornea; type II collagen in cartilage, invertebrate discs and vitreous bodies; type III collagen in fetal skin, the cardiovascular system and reticular fibers; type IV collagen in basement membranes; and type V collagen in the placenta and skin. Collagen types I, II and III are the most abundant forms and have a similar fibrillar structure. Type IV does not exist in fibrils but rather forms a two-dimensional reticulum constituting the principal component of the basal lamina.

A collagen gene is expressed to give a polypeptide termed a procollagen linked at its N-terminal to a signal peptide. The procollagen polypeptide contains a central segment that is ultimately found in mature collagen between N- and C-terminal propeptides. For procollagen $\alpha 1(I)$, the procollagen polypeptide is about 160 kDa, the mature collagen polypeptide about 90 kDa and the propeptides about 45 kDa. The signal peptide is linked to the amino end of the N-terminal propeptide. The amino acid composition of propeptides differs from the mature peptide. The mature peptide has an unusual repeating structure in which glycine occurs as nearly every third amino acid and there is a high proportion of proline residues. The propeptides have a role in promoting interchain assembly of procollagen chains into triplex structures.

Following expression of signal peptide-procollagen polypeptides, a series of posttranslation modifications occur in the course of assembly and secretion of procollagen. In fibroblasts, the following modifications have been identified: cleavage of signal peptides at the N-termini of the chains; hydroxylation of the Y-position proline and lysine residues; hydroxylation of a few X-position proline residues; addition of galactose or galactose and then glucose to some of the hydroxylysines, addition of a mannose-rich oligosaccharide to the C propeptides, association of the C-terminal propeptides through a process directed by a structure of these domains, formation of both intra and interchain disulfide bonds in the propeptides. Following these modifications, the procollagen chains assemble into a trimeric helix composed of three procollagen chains. In synthesis of some forms of collagen, the three procollagen chains are of the same type; in synthesis of other forms of collagen, the three procollagen chain are heterologous. For example, type I collagen contains two $\alpha 1(I)$ chains and one $\alpha 2(I)$ chain. Individual chains assemble into trimers by interactions of propeptides. These interactions include formation of both intrachain and interchain disulfide bonds in the propeptides.

On completion of processing and assembly, procollagen trimers are secreted from the cell and subject to further extracellular modifications. The N- and C-terminal propeptides are cleaved from the mature collagen peptide by specialized enzymes termed procollagen N-proteinase and procollagen C-proteinase. The cleavage reaction releases individual trimers of mature collagen having a molecular weight of about 285 kDa (termed tropocollagen). Individual trimers spontaneously assemble into higher order structures. These structures are then solidified by lysyl oxidase conversion of some lysine and hydroxylysine residues to aldehyde derivatives that form interchain crosslinks. The final product constitutes high molecular weight insoluble fibrils that can fulfill the natural and surgical structural roles noted above. In all, the modification process requires at least eight specific enzymes, and several nonspecific enzymes, and requires modification of over one hundred amino acids. See Prockop et al., *New England J. Med.* 311, 376–386 (1984) (incorporated by reference in its entirety for all purposes).

The utility of collagen in surgical processes has led to attempts to express recombinant collagen genes as a source of collagen. For example, a genomic DNA segment encoding human cartilage procollagen $\alpha 1(II)$ and a minigene version thereof (lacking most internal intronic sequences) have been expressed in 3T3 mouse fibroblast, a cell line producing endogenous collagen type I. See Ala-Kokko et al., *J. Biol. Chem*. 266, 14175–14178 (1991); Olsen et al., *J. Biol. Chem.* 266, 1117–11121 (1991)) (each of which is incorporated by reference in its entirety for all purposes). A cDNA encoding procollagen $\alpha 2(V)$ has been expressed in mouse fibroblasts expressing endogenous pro$\alpha 1(V)$. See Greenspan, *Proc. Natl. Acad. Sci. USA* 84, 8869–8873 (1987)) (incorporated by reference in its entirety for all purposes). Heterotrimers were deposited predominantly in the extracellular matrix of the cell layer. A cDNA encoding the human pro$\alpha 1(I)$ chain has been expressed in a human fibrosarcoma cell line producing endogenous collagen type IV. See Geddis & Prockop, *Matrix* 13, 399–405 (1993) (incorporated by reference in its entirety for all purposes). About two percent of transformed cell lines secreted homotrimeric pro$\alpha 1(I)$ chains. These chains were overmodified compared with normal pro$\alpha 1(I)$ chains as judged by SDS PAGE analysis. Transgenic mice exhibiting systemic expression of mutated forms of procollagen genes have also been reported. See Stacey et al., *Nature* (1988) 322, 131–136; Khillan et al., *J. Biol. Chem.* 266, 23373–23379 (1991); WO 92/22333. Most such mice were born dead or severely deformed.

Mammalian cellular expression systems are not entirely satisfactory for production of recombinant proteins because of the expense of propagation and maintenance of such cells. An alternative approach to production of recombinant proteins has been proposed by DeBoer et al., WO 91/08216, whereby recombinant proteins are produced in the milk of a transgenic animal. This approach avoids the expense of maintaining mammalian cell cultures and also simplifies purification of recombinant proteins.

Although the feasibility of expressing several recombinant proteins in the milk of transgenic animals has been demonstrated, it was unpredictable whether this technology could be extended to the expression of an multimeric protein requiring extensive posttranslational modification and assembly, such as collagen. Because mammary gland cells naturally produce only low levels of endogenous collagen type IV (David et al., *Expl. Cell. Res.* 170, 402–416 (1987)), it was uncertain whether these cells possessed the necessary complement and activity of enzymes for proper modification, assembly and secretion of other types of collagen, particularly, at high expression levels. If not properly modified, collagen might accumulate intracellularly rather than being secreted. Moreover, the large size of trimeric procollagen (>420 kDa) in comparison with other milk protein might have been expected to clog the secretory apparatus. The health and even viability of transgenic animals expressing exogenous collagen in their mammary glands was also uncertain. Inappropriate accumulation of collagen in the mammary gland might have impaired mammary gland development and resulted in cessation of lactation. Even low levels of secondary expression in tissues other than the mammary gland could have resulted in lethal accumulation of collagen deposits.

Notwithstanding the above uncertainties and difficulties, the invention provides inter alia healthy transgenic mammals secreting procollagen or collagen into their milk.

SUMMARY OF THE INVENTION

The invention provides transgenic nonhuman mammals useful for production of procollagen or collagen. The mammals have a transgene comprising a mammary-gland specific promoter, a mammary-gland specific enhancer; a secretory DNA segment encoding a signal peptide functional in mammary secretory cells of the transgenic mammal, and a recombinant DNA segment encoding an exogenous procollagen polypeptide. The recombinant DNA segment is operably linked to the secretory DNA segment to form a secretory-recombinant DNA segment which is, in turn, operably linked to the promoter and enhancer. In adult form, the nonhuman mammal bearing the transgene, or a female descendant of the mammal, is capable of expressing the secretory-recombinant DNA segment in the mammary secretory cells to produce a form of the exogenous procollagen polypeptide that is processed and secreted by the mammary secretory cells into milk as exogenous procollagen or collagen. Usually, the exogenous procollagen or collagen is secreted in trimeric form. The concentration of procollagen or collagen in the milk is usually about 100 $\mu$/ml and sometimes 1 mg/ml or more. The exogenous procollagen or collagen polypeptide is usually human, e.g., pro$\alpha$1 (I). The recombinant DNA segment can be cDNA, genomic or a hybrid. In some genomic DNA segments, a segment of the first intron is deleted to remove regulatory sequences. Some transgenic nonhuman mammals have a first transgene encoding a pro$\alpha$1(I) polypeptide and a second transgene encoding a pro$\alpha$2(I) polypeptide. The two transgenes are capable of being expressed to produce forms of $\alpha$1(I) and $\alpha$2(I) procollagen that are processed and secreted by the mammary secretory cells into milk as a trimer comprising at least one chain of $\alpha$1(I) procollagen or collagen and at least one chain of $\alpha$2(I) procollagen or collagen. Preferred species of transgenic mammals include bovine and murine.

In another aspect, the invention provides milk from transgenic nonhuman mammals as described above. The milk comprises procollagen or collagen.

The invention further provides transgenes for expressing procollagen or collagen. One such transgene comprises a casein promoter, a casein enhancer, a cDNA segment encoding a procollagen signal segment linked in-frame to a procollagen $\alpha$1(I) polypeptide, and a 3' flanking DNA segment from a gene encoding the procollagen polypeptide. The cDNA segment is operably linked at its 5' end to the promoter and the enhancer, and at its 3' end to the 3' flanking segment. Another transgene comprises a casein promoter, a casein enhancer and a genomic DNA segment comprising a segment from a 5' untranslated region to a 3' flanking region of a procollagen $\alpha$1(I) gene, operably linked to the promoter and the enhancer.

In a further aspect, the invention provides a stable mammary gland cell line having a transgene. The transgene comprises a mammary-gland specific promoter, a mammary-gland specific enhancer, a secretory DNA segment encoding a signal peptide functional in the cell line, and a recombinant DNA segment encoding an exogenous procollagen polypeptide operably linked to the secretory DNA segment to form a secretory-recombinant DNA segment, the secretory-recombinant DNA segment being operably linked to the promoter and to the enhancer. The cell line can be induced by a lactogenic hormone to express the transgene to produce a form of the exogenous procollagen polypeptide that is processed and secreted by the cell lines as exogenous procollagen or collagen in trimeric form.

Figure 1A:
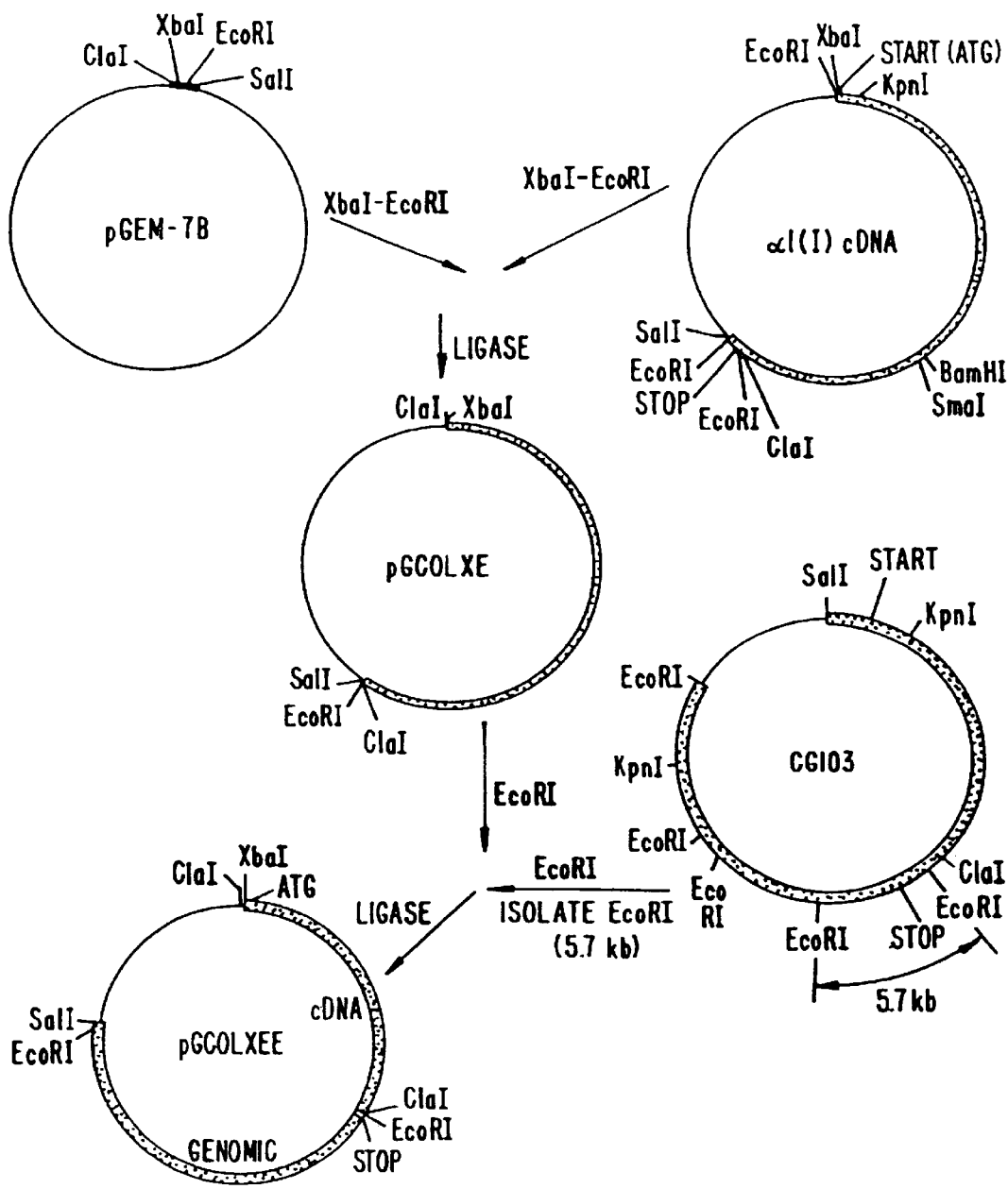
FIG. 1: Construction of a cDNA-genomic hybrid transgene for procollagen expression.

| Lane 1 | marker |
|---|---|
| Lane 2 | control, day 19 lactation |
| Lane 3 | founder 2399, day 4 lactation |
| Lane 4 | control, day 6 lactation |
| Lane 5 | founder 2395, day 4 lactation |
| Lane 6 | founder 2395, day 2 lactation |
| Lane 7 | control, day 3 lactation |
| Lane 8 | marker |
| Lane 9 | control, day 19 lactation |
| Lane 10 | founder 2399, day 4 lactation |
| Lane 11 | control, day 6 lactation |
| Lane 12 | founder 2395, day 4 lactation |
| Lane 13 | founder 2395, day 2 lactation |
| Lane 14 | control, day 3 lactation |
| Lane 15 | marker |

Figure 6:
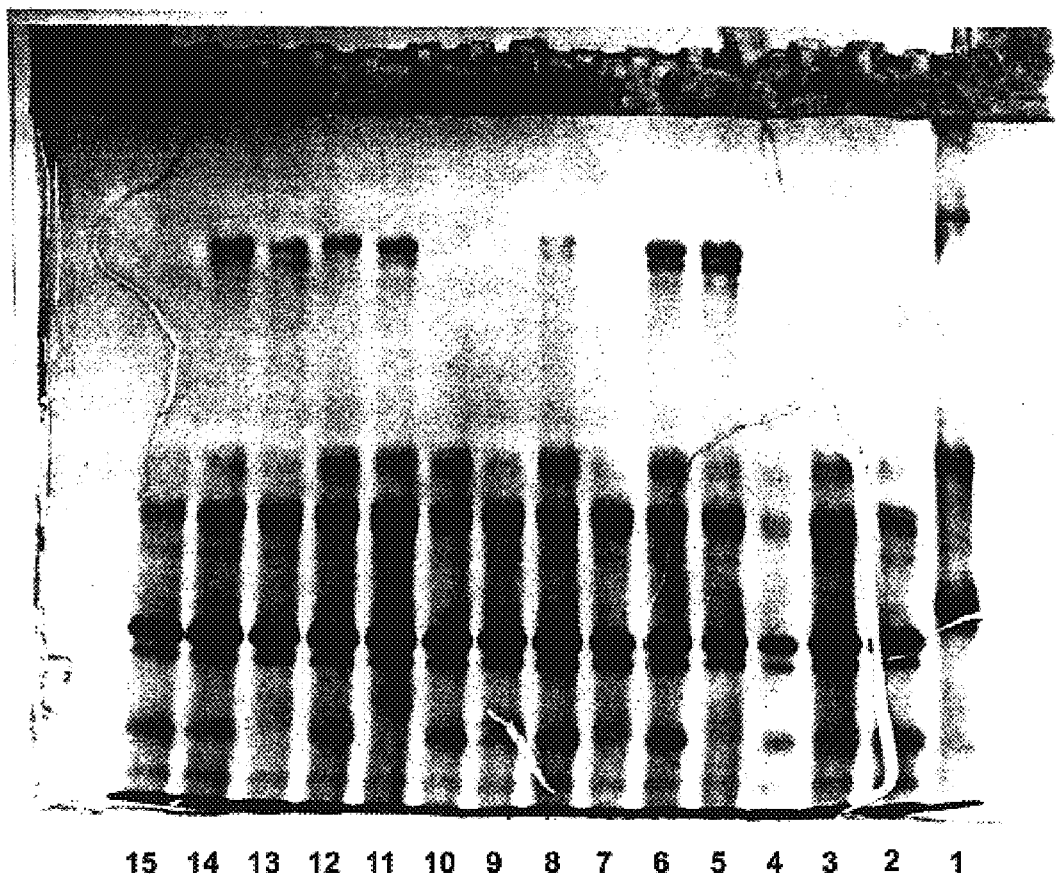

FIG. 6: SDS-PAGE analysis of milk proteins from additional transgenic mice under reducing conditions.

| Lane 1 | marker |
|---|---|
| Lane 2 | control, day 10 lactation |
| Lane 3 | founder 2393, day 4 lactation |
| Lane 4 | founder 2393, day 11 lactation |

-continued

| Lane 5 | founder 2395, day 4 lactation |
| Lane 6 | founder 2395, day 13 lactation |
| Lane 7 | founder 2399, day 4 lactation |
| Lane 8 | founder 2399, day 13 lactation |
| Lane 9 | founder 2400, day 5 lactation |
| Lane 10 | founder 2400, day 12 lactation |
| Lane 11 | founder 2406, day 4 lactation |
| Lane 12 | founder 2406, day 11 lactation |
| Lane 13 | founder 2411, day 5 lactation |
| Lane 14 | founder 2411, day 11 lactation |
| Lane 15 | control, day 10 lactation |

Figure 7A:
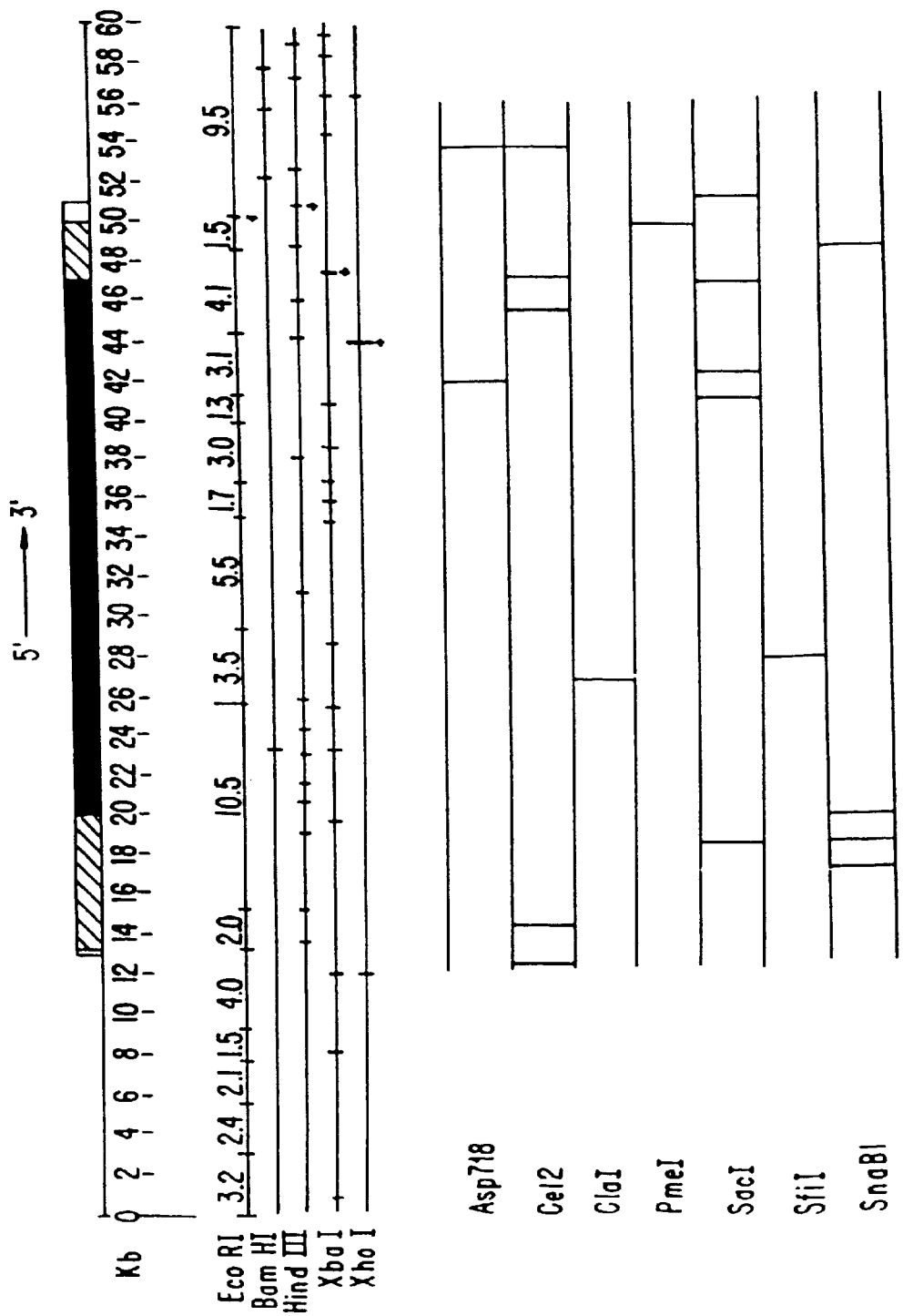
Figure 7B:
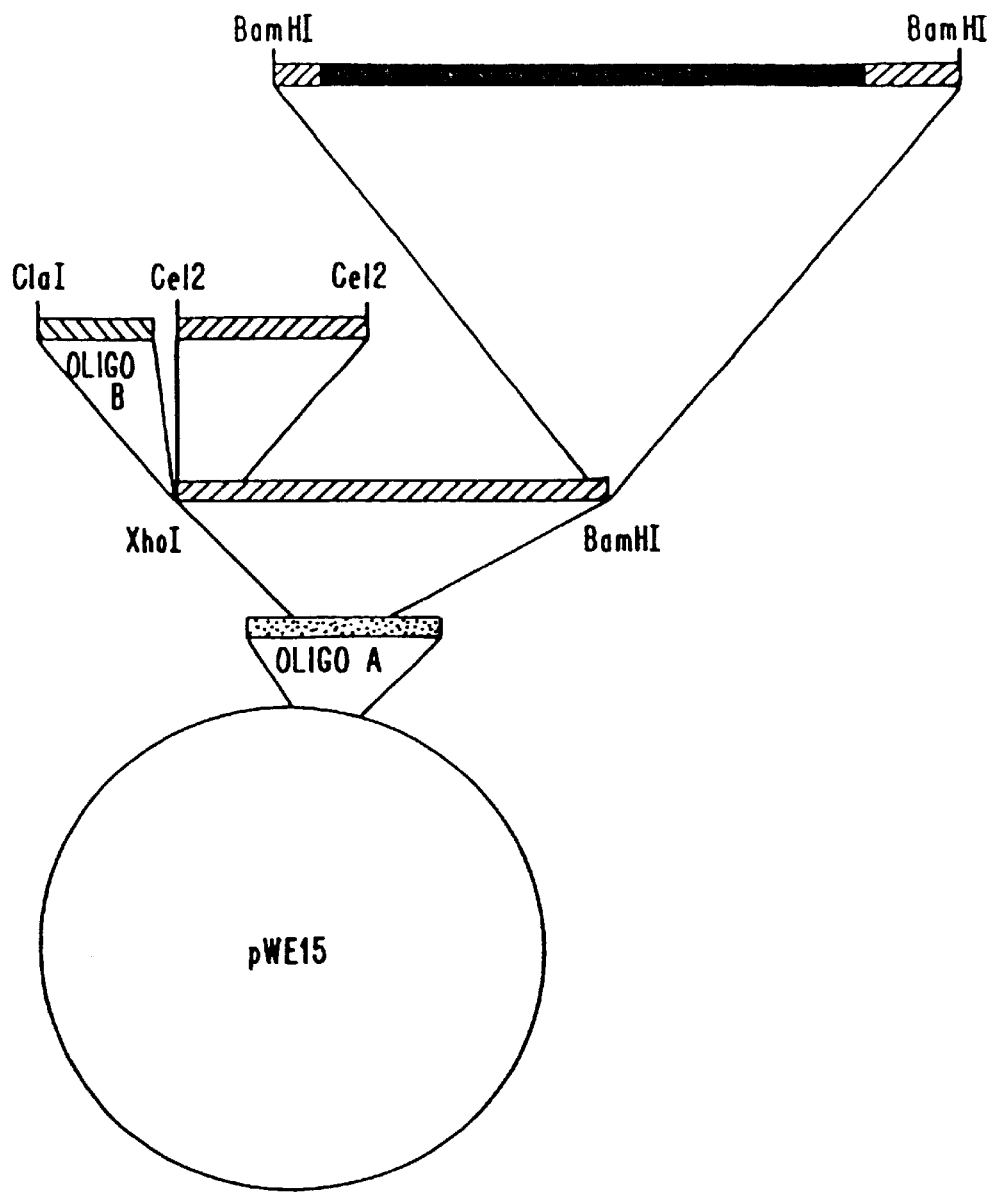

FIGS. 7(A–B): Construction of α2(I) procollagen expression vectors. Panel A shows the location of restriction sites in the αs1 gene. Panel B illustrates the steps in reconstructing the 5' end of the α2(I) gene in which the 5' untranslated sequence from the collagen gene is replaced with the 5' untranslated sequence from the bovine αs1 casein gene. Panel B also show the step of ligating the reconstructed 5' end fragment to a BamHI-BamHI fragment containing the rest of the gene. Panel C (lower) shows the restriction sites in the reconstructed α2(I) gene resulting from these steps. Panel C (upper) shows the restriction sites in a reconstructed α2(I) gene resulting from a second strategy in which the BamHI-BamHI fragment is replaced with a BamH1-XhoI fragment and an XhoI-XhoI fragment from the α2(I) procollagen gene.

Figure 8:
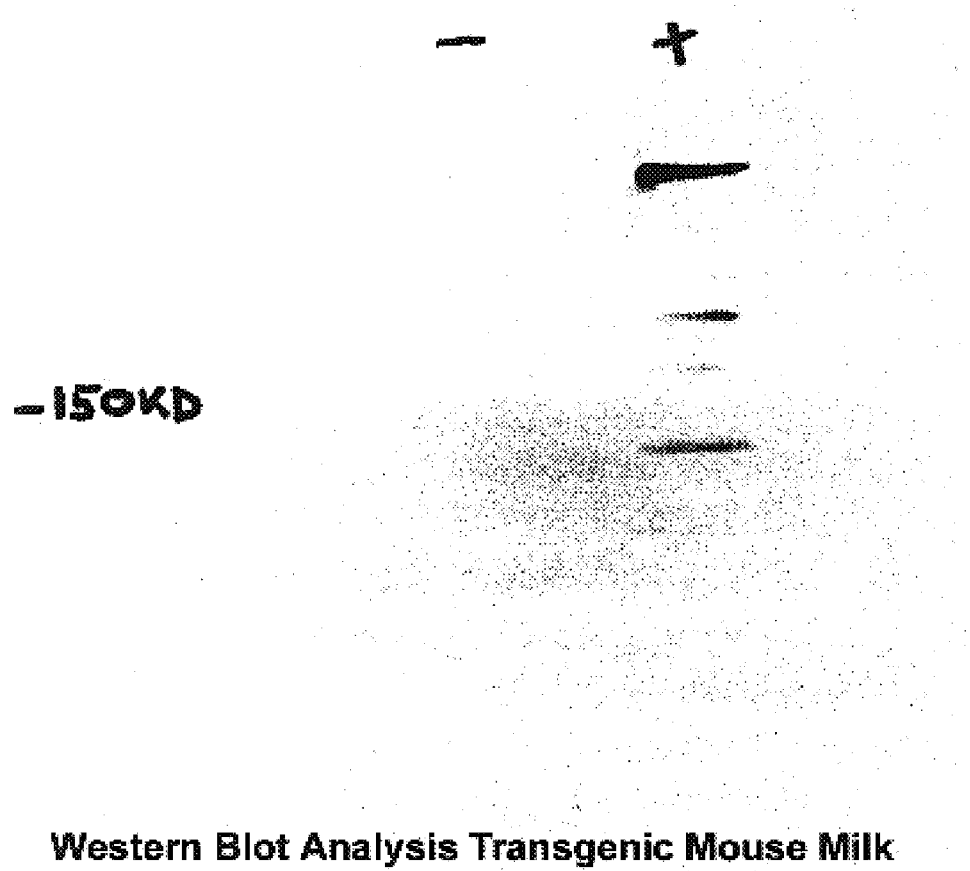

FIG. 8: Western blot of milk from a transgenic mouse harboring a procollagen α1(I) transgene.

Figure 9:
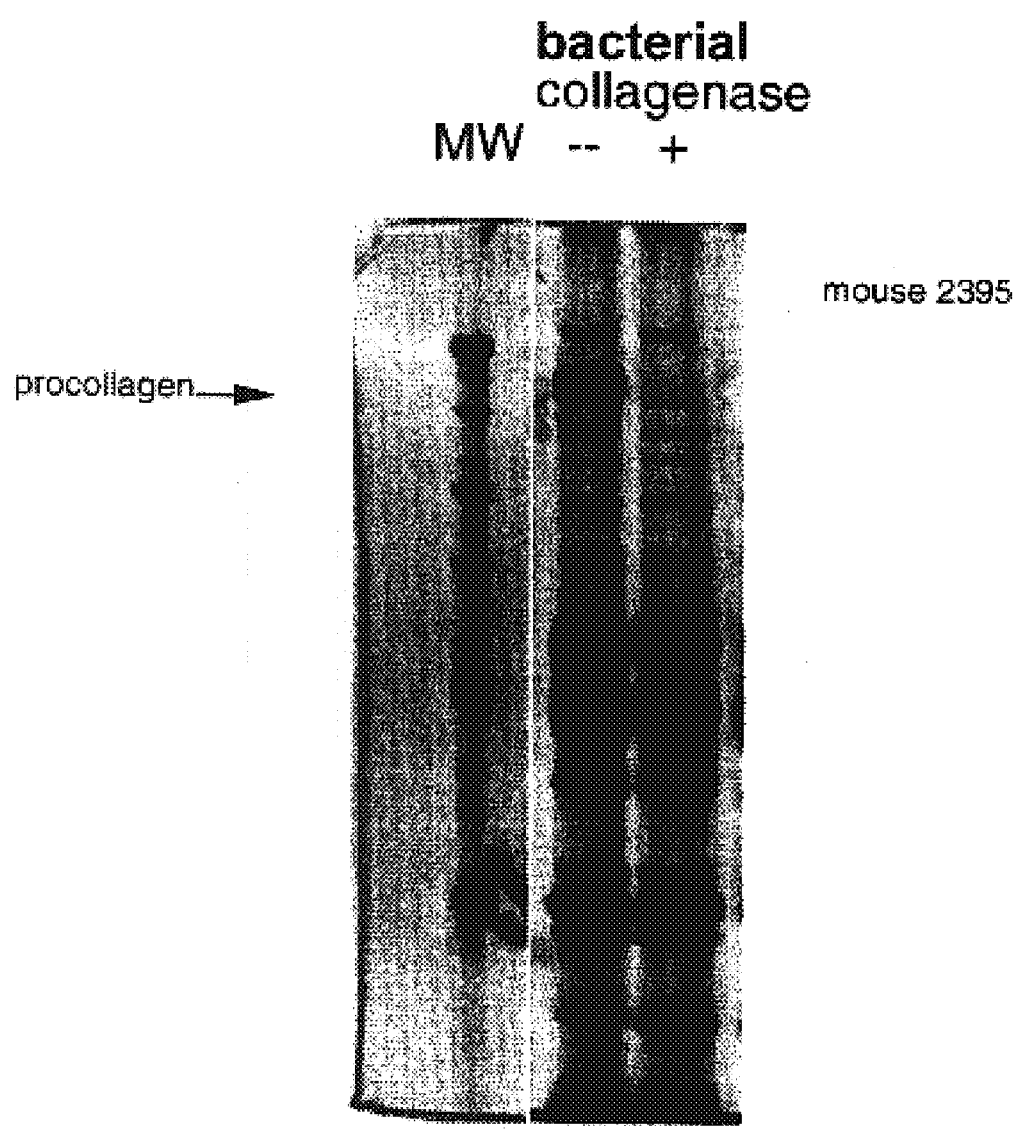

FIG. 9: Collagenase digestion of milk from a transgenic mouse harboring a procollagen α1(I) transgene.

Figure 10A:
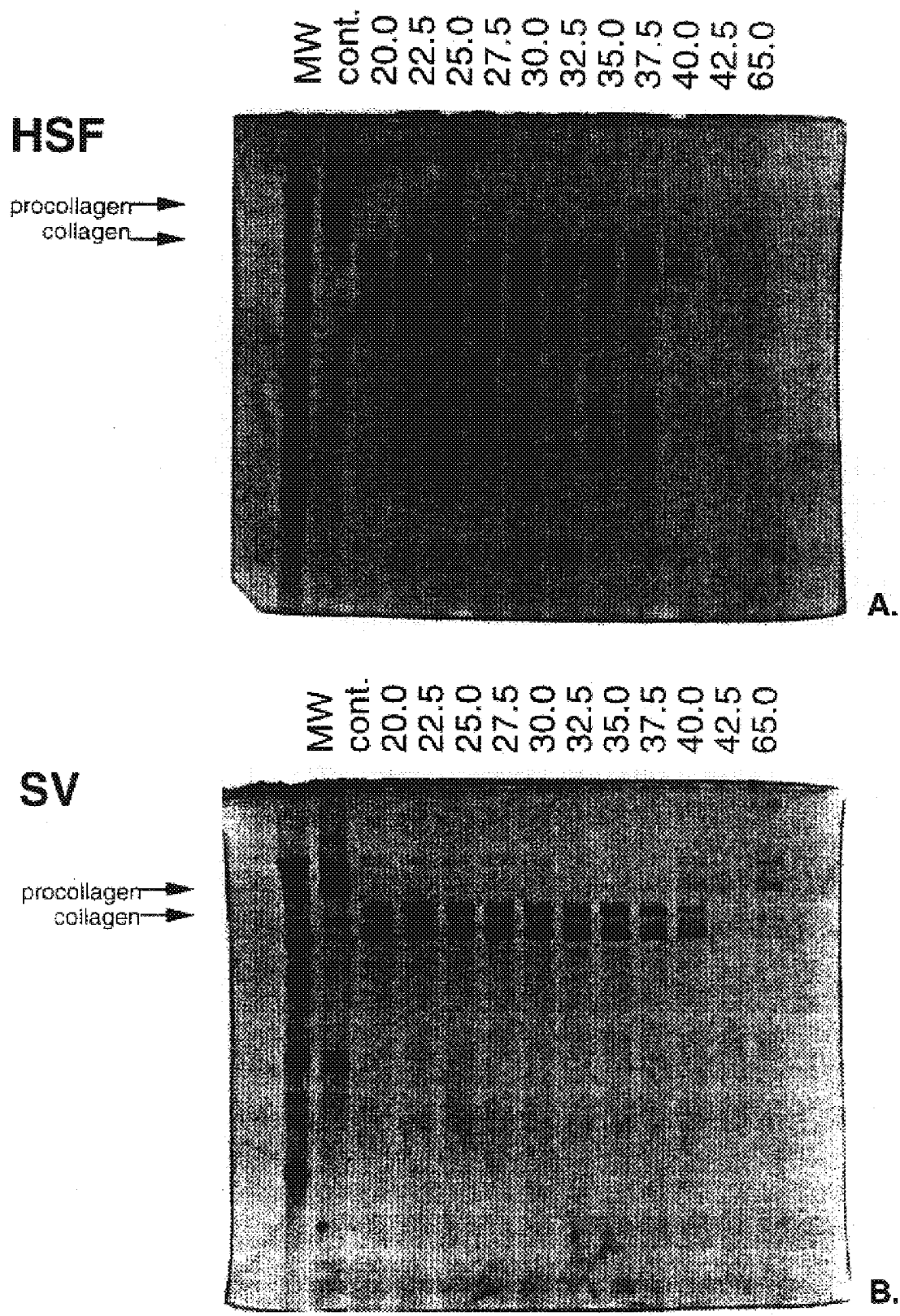
Figure 10B:
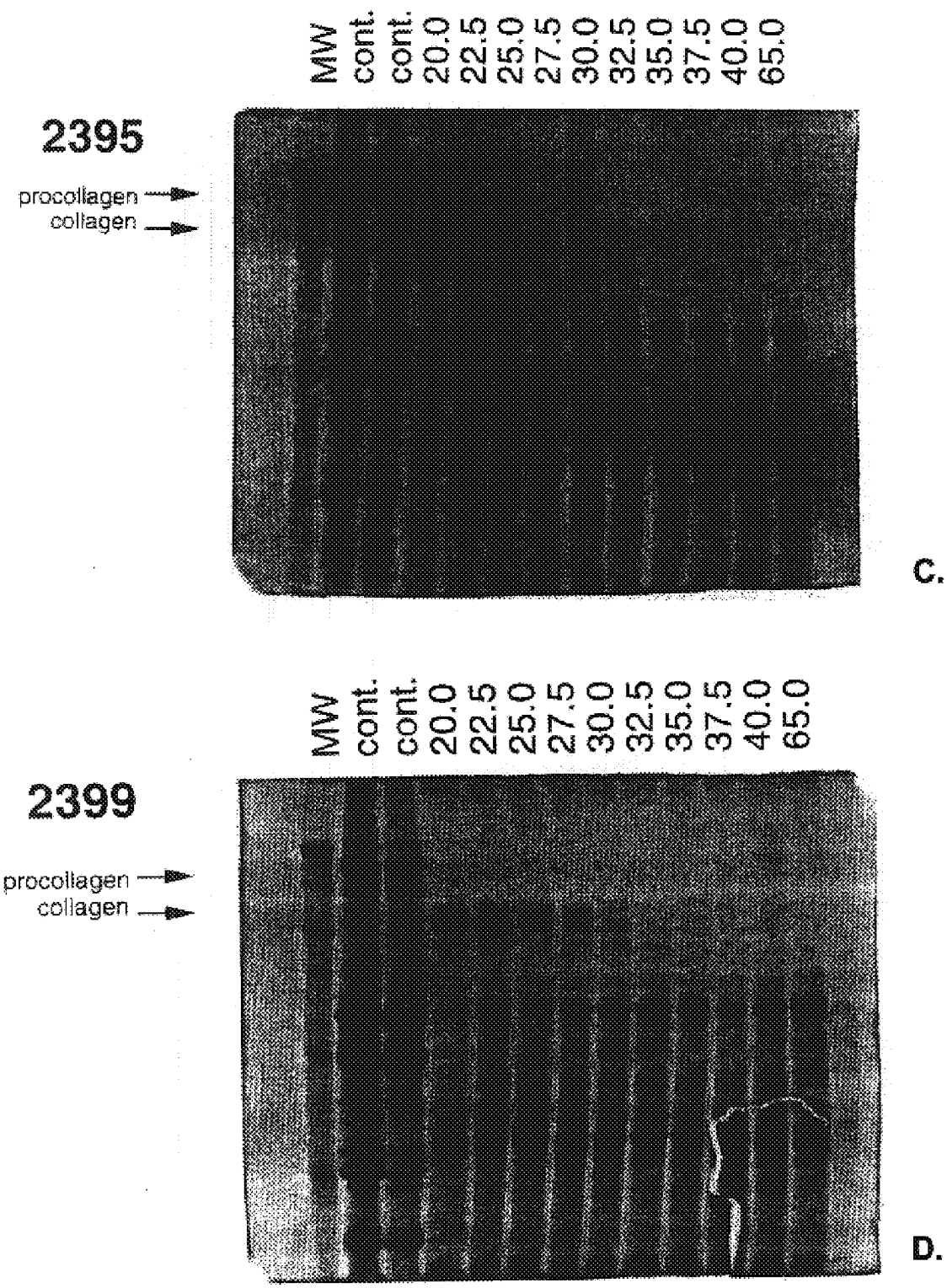

FIGS. 10(A–D) Thermal stability of procollagen in milk from transgenic mice. Panels A, B, C and D show samples from human skin fibroblasts (HSV) (expressing natural procollagen type I), human lung fibroblasts (SV) (encoding human procollagen α1(I), milk from mouse 2395 (a high expresser) and milk from mouse 2399 (a medium expresser). The numbers above each gel indicate the temperature of digestion. Control samples were incubated at 20° C. without trypsin or chymotrypsin.

Figure 11:
Figure 11:

FIG. 11: Northern blot of RNA from various tissues in a transgenic mouse harboring a transgene expressing homotrimeric procollagen α1(I).

DEFINITIONS

The term "substantial identity"or "substantial homology" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity). Preferably, residue positions which are not identical differ by conservative amino acid substitutions.

The term "substantially pure" or "isolated" means an object species has been identified and separated and/or recovered from a component of its natural environment. Usually, the object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent by weight of all macromolecular species present in the composition. Most preferably, the object species is purified to essential homogeneity (contaminant species cannot be detected in the composition by conventional detection methods) wherein the composition consists essentially of a single macromolecular species.

A DNA segment is operably linked when placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

An exogenous DNA segment is one foreign to the cell or homologous to the cell but in a position within the host cell nucleic acid in which the element is not ordinarily found. Exogenous DNA segments are expressed to yield exogenous polypeptides.

DETAILED DESCRIPTION

The invention provides transgenic nonhuman mammals secreting procollagen or collagen into their milk. Secretion is achieved by incorporation of a transgene encoding a procollagen gene and regulatory sequences capable of targeting expression of the gene to the mammary gland. The procollagen gene is expressed, posttranslationally modified and assembled into procollagen within the mammary gland. Procollagen is secreted into the milk, usually in trimeric form. Usually, further processing of trimeric procollagen does not spontaneously occur following secretion into milk.

A. Collagen Genes

The invention provides transgenic nonhuman mammals expressing DNA segments containing any of the more than 23 known collagen genes. See Adams et al., *Am. J. Respir. Cell. Molec. Biol.* 1, 161–168 (1989) (incorporated by reference in its entirety for all purposes). Polypeptides can be expressed individually giving rise to homopolymers or in combinations, giving rise to heteropolymers. Expression of a DNA segment or segments that produce collagen having the same constituent chains as a naturally occurring form of collagen is preferred. The most common types found in interstitial tissues are types I, III, V and VI, whereas types II, IX, X and XI predominate in cartilage. Some of these types exist natively as homotriplexes; others are heterotriplexes. The nomenclature designates the genetic origin of a particular collagen. For example, type I collagen is a heterotriplex containing the products of two different collagen-encoding genes. This type of collagen is designated $[\alpha1(I)]_2 \alpha2(I)$; thus, type I collagen triplexes contain two chains encoded by the procollagen α1(I) gene and one protein chain encoded by the pro α2(I) gene. Type II collagen is designated $[\alpha_1(II)]_3$ comprising a homotrimer of α1(II) polypeptides. Type III collagen is also a homotrimer designated $[\alpha1(III)]_3$. Type IV and type V collagens are heterotrimers, respectively designated $[\alpha1(IV)]_2\alpha2(IV)$ and $[\alpha1(V)]_2\alpha2(V)$. Transgenic mammals expressing allelic, cognate; nonallelic and induced variants of any of the known collagen coding sequences are also included. Such variants usually show substantial sequence identity at the amino acid level with known procollagen genes particularly in the collagen encoding domains of such genes. Such variants usually hybridize to a known gene under stringent conditions or crossreact with antibodies to a polypeptide encoded by one of the known genes.

DNA clones containing the genomic or cDNA sequences of many of the known procollagen genes are available. Barsh et al., *J. Biol. Chem.* 259, 14906–14913 (1984) and Chu et al., *Nucleic Acid Res.* 10, 5925–5933 (1982) (incorporated by reference in their entirety for all purposes), respectively describe genomic and cDNA clones encoding the proα1(I) gene. See also Tromp et al., *Biochem J.* 253, 9191–922 (1988). Chu et al., *J. Biol. Chem.* 260, 4357–4363 (1985) (incorporated by reference in its entirety for all purposes) describe a clone of a proα1(III) gene. Dewet et al., *J. Biol. Chem.* 262, 16032–16036 (incorporated by reference in its entirety for all purposes) describe the cloning of the human proα2(I) gene. sangiorgi et al., *Nucleic Acids Res.* 13, 2207–2225 (1985) and Elima et al., *Biochem. J.* 229, 183–188 (1985) (incorporated by reference in their entirety for all purposes) describe genomic and cDNA clones of human proα1(II). Other examples of genomic and cDNA sequences are available from GenBank. To the extent that additional cloned sequences of collagen genes are required, they may be obtained from genomic or cDNA libraries (preferably human) using known collagen DNA sequences or antibodies to known collagen polypeptides as probes.

B. Collagen Conformation

Recombinant collagen or procollagen polypeptides are preferably processed and assembled to have the same or similar trimeric structure as naturally occurring collagens. In this structure, each individual strand forms a helix and the three strands wrap around each other to form a superhelical cable. In mature collagen, the superhelical cable contains short nonhelical extensions designated telopeptides. In procollagen, the nonhelic regions are longer comprising the telopeptides linked to propeptides. A homotrimer contains three identical strands; a heterotrimer contains at least two different type of collagen chain, and usually contains two copies of a first type and one copy of a second type. The rise per residue in the superhelix is about 2.9 Å and the number of residues per turn is about 3.3 in the case of type I collagen. The trimeric structure is stabilized in part by hydrogen bonding of modified residues (e.g., hydroxyproline) introduced by posttranslational processing. Thus, the assembly of a trimeric structure indicates that at least substantially complete posttranslational processing has occurred. Unless an appropriate number of Y-position prolyl residues are hydroxylated to 4-hydroxyproline by prolyl 4-hydroxylase, the newly synthesized chains cannot fold in to a triple-helical formation, are poorly secreted and cannot self-assemble into collagen fibrils. See Prockop et al., WO 92/22333. The extent of posttranslational modification can be more precisely determined by SDS-page analysis in comparison with naturally occurring collagen. The greater the extent of posttranslational modification the less the mobility of the monomeric chain under this analysis.

The existence of trimeric procollagen or collagen can be detected by resistance to trypsin or chymotrypsin digestion. Thermal stability and thereby proper folding can be determined from resistance to proteolytic digestion as a function of temperature. See Bruckner & Prockop, *Annal. Biochem.* 110, 36–368 (1981) (incorporated by reference in its entirety for all purposes). As the melting point of the triple helix is exceeded (41 degrees for collagen type 1), the rate of protease digestion greatly increases. Usually, the procollagen or collagen produced by the transgenic animals of the invention has a melting point in the range of about 25–45° C. and more usually about 30–40° C. Trimeric procollagen or collagen can also be identified by the presence of high molecular weight bands (about 420 kDa for procollagen type I and about 285 kDa for collagen type I) on nonreducing gels.

C. Transgene Design

Transgenes are designed to target expression of a recombinant protein (usually a procollagen polypeptide) to the mammary gland of a transgenic nonhuman mammal harboring the transgene. The basic approach entails operably linking a an exogenous DNA segment encoding a procollagen polypeptide with a signal sequence, a promoter and an enhancer. The DNA segment can be genomic, minigene (genomic with one or more introns omitted), cDNA, a YAC fragment, a chimera of two different collagen genes, or a hybrid of any of these. Inclusion of genomic sequences generally leads to higher levels of expression. Very high levels of expression might overload the capacity of the mammary gland to perform posttranslation modifications, assembly and secretion of procollagen chains. However, the results presented in Example 3 indicate that substantial posttranslational modification occurs notwithstanding a high expression level in the mg/ml range. Thus, genomic constructs or hybrid cDNA-genomic constructs are generally preferred.

In genomic constructs, it is not necessary to retain all intronic sequences. Some such sequences, notably the first intron of α1(I) procollagen may contain a segment of regulatory sequences whose removal is desirable. Other intronic sequences can be removed to obtain a smaller transgene facilitating DNA manipulations and subsequent microinjection. See Archibald et al., WO 90/05188 (incorporated by reference in its entirety for all purposes). It is also possible to delete portions of noncoding exons (e.g., a 5' portion of exon 1 of the α1(I) procollagen gene) forming three dimensional structures in the mRNA impeding transcription. Removal of some introns is also useful in some instances to reduce expression levels and thereby ensure that posttranslational modification is substantially complete. In some transgenes, selected nucleotides in procollagen sequences are mutated to remove proteolytic cleavage sites recognized by N- and C- procollagen peptidases. Removal of such sites prevents spontaneous conversion of procollagen to collagen (although Example 3 indicates that such conversion is usually substantially absent even without these mutations). In some transgenes, a nucleotide encoding a recognition site to collagenase enzyme (Gly-Ile or Gly-Leu) is mutagenized as a precaution against digestion of procollagen after secretion into milk. See Wu et al., *Proc. Natl. Acad. Sci.* (*USA*) 87, 5888–5892 (1990) (incorporated by reference in its entirety for all purposes).

The species from which the DNA segment encoding a procollagen sequence is obtained will usually depend on the intended use of the procollagen. Where the intended use is in human surgery it is preferred that the DNA segment be of human origin to minimize subsequent immune response in the recipient human patient. Analogously if the intended use were in veterinary surgery (e.g., on a horse, dog or cat), it is preferable that the DNA segment be from the same species.

The promoter and enhancer are from a gene that is exclusively or at least preferentially expressed in the mammary gland (i.e., a mammary-gland specific gene). Preferred genes as a source of promoter and enhancer include β-casein, κcasein, αs1-casein, αs2-casein, β-lactoglobulin, whey acid protein, and α-lactalbumin. The promoter and enhancer are usually but not always obtained from the same mammary-gland specific gene. This gene is preferably from the same species of mammal as the mammal into which the transgene is to be inserted. Expression regulation sequences from other species such as those from human genes can also be used. The signal sequence must be capable of directing the secretion of procollagen from the mammary gland. Suitable signal sequences can be derived from virtually any mammalian gene encoding a secreted protein. Preferred sources of signal sequences are the signal sequence naturally linked to the procollagen DNA segment being expressed, or a signal sequence from the same gene as the promoter and enhancer are obtained. Optionally, additional regulatory sequences are included in the transgene to optimize expression levels. Such sequences include 5' flanking regions, 5' transcribed but untranslated regions, intronic sequences, 3' transcribed but untranslated regions, polyadenylations sites, 3' flanking regions. Such sequences are usually obtained either from the mammary-gland specific gene from which the promoter and enhancer are obtained or from the procollagen gene being expressed. Inclusion of such sequences produces a genetic milieu simulating that of an authentic mammary gland specific gene and/or that of an authentic procollagen gene. This genetic milieu results in some cases (e.g., bovine αS1-casein) in higher expression of the transcribed procollagen gene. Alternatively, 3' flanking regions and untranslated regions are obtained from other heterologous genes such as the β-globin gene or viral genes. The inclusion of 3' and 5' untranslated regions from the procollagen, mammary specific gene, or other heterologous gene can also increase the stability of the transcript.

In some embodiments, about 0.5, 1, 5, 10, 15, 20 or 30 kb of 5' flanking sequence is included from a mammary specific gene in combination with about 1, 5, 10, 15, 20 or 30 kb or 3' flanking sequence from the procollagen gene being expressed. If the procollagen polypeptide is expressed from a cDNA sequence, it is advantageous to include an intronic sequence between the promoter and the coding sequence. The intronic sequence is preferably a hybrid sequence formed from a 5' portion from an intervening sequence from the first intron of the mammary gland specific region from which the promoter is obtained and a 3' portion from an intervening sequence of an IgG intervening sequence or a procollagen gene. See DeBoer et al. WO 91/08216 (incorporated by reference in its entirety for all purposes).

A preferred transgene for expressing procollagen or collagen comprises a cDNA-genomic hybrid procollagen gene linked 5' to a casein promoter and enhancer. The hybrid procollagen gene includes the signal sequence, procollagen coding region, and a 3' flanking region. The transgene is conveniently assembled from three components: a 5' flanking sequences from a casein gene containing the casein promoter and enhancer; a cDNA segment encoding the signal sequence and procollagen polypeptide and a genomic segment proving the 3' flanking region. The casein fragment is linked to the cDNA segment by fusion of 5' untranslated regions of the casein and procollagen genes. The cDNA segment is linked to the genomic segment by a fusion within the last exon (exon 52) of the procollagen coding sequence. Optionally, the cDNA segment includes an intronic sequence between the 5' casein and procollagen untranslated regions. Of course, corresponding cDNA and genomic segments can also be fused at other locations within the gene provided a contiguous protein can be expressed from the resulting fusion. Depending on the site of fusion, the construct will contain anywhere from 0 to 51 introns.

Other preferred transgenes have a genomic procollagen segment linked 5' to casein regulatory sequences. The genomic segment is usually contiguous from the 5' untranslated region to the 3' flanking region of the procollagen gene, except that a segment of the first intron is sometimes deleted to remove control sequences. Thus, the genomic segment includes a portion of the procollagen 5' untranslated sequence, the signal sequence, alternating introns and coding exons, a 3' untranslated region, and a 3' flanking region. The genomic segment is linked via the 5' untranslated region to a casein fragment comprising a promoter and enhancer and usually a 5' untranslated region. In some constructs, all of the procollagen 5' untranslated sequence is replaced with the casein 5' untranslated sequence.

DNA sequence information is available for all of the mammary gland specific genes listed above, in at least one, and often several organisms. See, e.g., Richards et al., *J. Biol. Chem.* 256, 526–532 (1981) (α-lactalbumin rat); Campbell et al., *Nucleic Acids Res.* 12, 8685–8697 (1984) (rat WAP); Jones et al., *J. Biol. Chem.* 260, 7042–7050 (1985)) (rat β-casein); Yu-Lee & Rosen, *J. Biol. Chem.* 258, 10794–10804 (1983) (rat γ-casein)); Hall, *Biochem. J.* 242, 735–742 (1987) (α-lactalbumin human); Stewart, *Nucleic Acids Res.* 12, 389 (1984) (bovine αs1 and κ casein cDNAs); Gorodetsky et al., *Gene* 66, 87–96 (1988) (bovine β casein); Alexander et al., *Eur. J. Biochem.* 178, 395–401 (1988) (bovine κ casein); Brignon et al., *FEBS Lett.* 188, 48–55 (1977) (bovine αS2 casein); Jamieson et al., *Gene* 61, 85–90 (1987), Ivanov et al., *Biol. Chem.* Hoppe-Seyler 369, 425–429 (1988), Alexander et al., *Nucleic Acids Res.* 17, 6739 (1989) (bovine β lactoglobulin); Vilotte et al., *Biochimie* 69, 609–620 (1987) (bovine α-lactalbumin) (incorporated by reference in their entirety for all purposes). The structure and function of the various milk protein genes are reviewed by Mercier & Vilotte, *J. Dairy Sci.* 76, 3079–3098 (1993) (incorporated by reference in its entirety for all purposes). To the extent that additional sequence data might be required, sequences flanking the regions already obtained could be readily cloned using the existing sequences as probes. Mammary-gland specific regulatory sequences from different organisms are likewise obtained by screening libraries from such organisms using known cognate nucleotide sequences, or antibodies to cognate proteins as probes.

General strategies and exemplary transgenes employing αs1-casein regulatory sequences for targeting the expression of a recombinant protein to the mammary gland are described in more detail in WO 91/08216 and WO 93/25567 (incorporated by reference in their entirety for all purposes). Examples of transgenes employing regulatory sequences from other mammary gland specific genes have also been described. See, e.g., Simon et al., *Bio/Technology* 6, 179–183 (1988) and WO88/00239 (1988) (β-lactoglobulin regulatory sequence for expression in sheep); Rosen, EP 279,582 and Lee et al., *Nucleic Acids Res.* 16, 1027–1041 (1988) (β-casein regulatory sequence for expression in mice); Gordon, *Biotechnology* 5, 1183 (1987) (WAP regulatory sequence for expression in mice); WO 88/01648 (1988) and *Eur. J. Biochem.* 186, 43–48 (1989) (α-lactalbumin regulatory sequence for expression in mice) (incorporated by reference in their entirety for all purposes).

Some transgenic mammals express more than one procollagen gene. Such transgenes are usually constructed independently, each according to the principles discussed above for a single transgene. Coinjection of the two transgenes often results in cointegration and thereby coordinate expression of the transgenes. Coordinate expression can also be obtained by placing two procollagen genes under the coordinate control of the same regulatory sequences. This is achieved by linking the segments encoding the procollagen inframe through a proteolytic cleavage site. The procollagens are expressed as a fusion protein that is separated into its component parts by an intracellular proteolytic enzyme. Alternatively, two independent transcriptional units can be produced, each encoding a procollagen gene, and the two units joined to form a single transgene.

In some embodiments of the invention, additional transgenes are constructed for targeting expression of enzymes involved in posttranslation processing to the mammary gland. The data presented in Example 3 indicate that surprisingly mammary glands already express these enzymes at sufficient quantities to obtain assembly and secretion of trimeric procollagen chains at high levels. However, in some transgenic mammals expressing procollagen at high levels, it is sometimes preferable to supplement endogenous levels of processing enzymes with additional enzyme resulting from transgene expression. Such transgenes are constructed employing similar principles to those discussed above with the processing enzyme coding sequence replacing the procollagen coding sequence in the transgene. It is not generally necessary that posttranslational processing enzymes be secreted. Thus, the secretion signal sequence linked to procollagen sequence is replaced with a signal sequence that targets the processing enzyme to the endoplasmic reticulum without secretion. For example, the signal sequences naturally associated with these enzymes are suitable. Genes involved in posttranslation modifications and assembly protein disulfide isomerase, which combines with the alpha subunit of prolyl hydroxylase to form a tetrameric protein isolated as prolyl hydroxylase. The cloned gene for protein disulfide isomerase is available (Tasanen et al., *J Biol Chem* (1988) 263, 16218–16224) (incorporated by reference in its entirety for all purposes). The cDNA for the alpha subunit has also been cloned from chickens and humans. See Bassuk et al., *Proc. Natl. Acad. Sci. USA* (1989) 86, 7382–7386; Helaakoski, T., *Proc Natl Acad Sci USA* (1989) 86, 4392–4396 (incorporated by reference in their entirety for all purposes). A clone encoding the human lysyl oxidase gene is reported by Hanaleinen et al., *Genomics* 17, 544–548 (1993) (incorporated by reference in its entirety for all purposes). Some transgenes encode a copy of bik, a cellular protein reported to facilitate secretion.

The observation that the transgenic mammal of the invention principally secrete procollagen rather than processed collagen (see Example 3) suggests that enzymes having roles in postsecretional processing steps (e.g., N- and C-terminal proteases) are not produced by mammary secretory cells in sufficient proportions to complete processing of the recombinant collagen. The substantial absence of these enzymes is potentially advantageous because it allows postsecretional processing, which initiates formation of insoluble aggregates, to be controlled (see infra). Thus, in general, there is no need to produce transgenes for expression of postsecretional enzymes.

In embodiments where multiple transgenes are constructed for insertion into the same mammal, the regulatory sequences, while selected according to the same principles, need not be the same in each instance. For example, one transgene for expression of a first procollagen DNA segment might include regulatory sequences from a αs1 casein gene. A second transgene for inclusion in the same animal would usually contain the second procollagen DNA segment linked to regulatory sequences from an αs1 casein gene. However, the second procollagen DNA segment could also be linked to regulatory sequences from another milk protein gene, such as an whey acidic protein gene.

D. Transgenesis

The transgenes described above are introduced into nonhuman mammals. Most nonhuman mammals, including rodents such as mice and rats, rabbits, ovines such as sheep and goats, porcines such as pigs, and bovines such as cattle and buffalo, are suitable. However, nonviviparous mammals such as a spiny anteater or duckbill platypus are typically not employed. In some methods of transgenesis, transgenes are introduced into the pronuclei of fertilized oocytes. For some animals, such as mice fertilization is performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits a transgene to be introduced into substantially synchronous cells at an optimal phase of the cell cycle for integration (not later than S-phase). Transgenes are usually introduced by microinjection. See U.S. Pat. No. 4,873,292. Fertilized oocytes are then cultured in vitro until a pre-implantation embryo is obtained containing about 16–150 cells. The 16–32 cell stage of an embryo is described as a morula. Pre-implantation embryos containing more than 32 cells are termed blastocysts. These embryos show the development of a blastocoel cavity, typically at the 64 cell stage. Methods for culturing fertilized oocytes to the pre-implantation stage are described by Gordon et al. (1984) *Methods Enzymol.* 101, 414; Hogan et al., *Manipulation of the Mouse Embryo: A Laboratory Manual,* C.S.H.L. N.Y. (1986) (mouse embryo); and Hammer et al. (1985) *Nature* 315, 680 (rabbit and porcine embryos); Gandolfi et al. (1987) *J. Reprod. Fert.* 81, 23–28; Rexroad et al. (1988) *J. Anim. Sci.* 66, 947–953 (ovine embryos) and Eyestone et al. (1989) *J. Reprod. Fert.* 85, 715–720; Camous et al. (1984) *J. Reprod. Fert.* 72, 779–785; and Heyman et al. (1987) *Theriogenology* 27, 5968 (bovine embryos) (incorporated by reference in their entirety for all purposes). Sometimes pre-implantation embryos are stored frozen for a period pending implantation. Pre-implantation embryos are transferred to an appropriate female resulting in the birth of a transgenic or chimeric animal depending upon the stage of development when the transgene is integrated. Chimeric mammals can be bred to form true germline transgenic animals.

Alternatively, transgenes can be introduced into embryonic stem cells (ES). These cells are obtained from preimplantation embryos cultured in vitro. Bradley et al. (1984), *Nature* 309, 255–258 (incorporated by reference in its entirety for all purposes). Transgenes can be introduced into such cells by electroporation or microinjection. Transformed ES cells are combined with blastocysts from a nonhuman animal. The ES cells colonize the embryo and in some embryos form the germ line of the resulting chimeric animal. See Jaenisch, *Science,* 240, 1468–1474 (1988) (incorporated by reference in its entirety for all purposes). Alternatively, ES cells can be used as a source of nuclei for transplantation into an enucleated fertilized oocyte giving rise to a transgenic mammal.

For production of transgenic animals containing two or more transgenes, the transgenes can be introduced simultaneously using the same procedure as for a single transgene. Alternatively, the transgenes can be initially introduced into separate animals and then combined into the same genome by breeding the animals. Alternatively, a first transgenic animal is produced containing one of the transgenes. A second transgene is then introduced into fertilized ova or embryonic stem cells from that animal. In some embodiments, transgenes whose length would otherwise exceed about 50 kb, are constructed as overlapping fragments. Such overlapping fragments are introduced into a fertilized oocyte or embryonic stem cell simultaneously and undergo homologous recombination in vivo. See Kay et al., WO 92/03917 (incorporated by reference in its entirety for all purposes).

E. Characteristics of Transgenic Mammals

Transgenic mammals of the invention incorporate at least one transgene and sometimes several transgenes in their genome as described above. The transgene(s) target expression of procollagen DNA segments at least predominantly to the mammary gland. Surprisingly, the mammary glands are capable of expressing enzymes required for posttranslation modification of collagen in great excess with respect to the processing capacity needed for endogenous collagen synthesis. Processing by enzymes in the mammary gland results in substantially complete posttranslational modification of exogenous procollagen polypeptides at least to the extent that trimers of procollagen are formed and secreted. Hydroxylation of proline residues may in some instances be increased by supplementing the diet of transgenic animals with Vitamin C. This is especially desirable when the transgenic animal is fed on a food mix lacking endogenous Vitamin C. Vitamin C is supplemented at a level of about 50–1000 mg/kg food or preferably about 200 mg/kg food. Endogenous collagen produced by the mammary gland is of type IV and is therefore routed to the basement membrane. Thus, the secreted procollagen is substantially or entirely free from endogenous procollagen and collagen (i.e., endogenous collagen forms less than 10, 20 or 50% of total secreted collagen). Usually, the secreted polypeptide is predominantly in the procollagen form and remains in that form until proteinase(s) are supplied exogenously. The proteinase can be the procollagen N- and C-terminal proteases employed in vivo or nonspecific proteolytic enzymes. The trimeric portion of a procollagen triple helix is relatively resistant to proteases. Thus, the propeptides are digested first by nonspecific proteases leaving trimeric collagen. In some transgenic animals, endogenous proteases are secreted resulting in spontaneous processing of procollagen to collagen following secretion.

Procollagen or collagen is secreted at high levels of at least 10, 50, 100, 500, 1000, 2000, 5000 or 10,000 µg/ml. Surprisingly, the transgenic mammals of the invention exhibit substantially normal health. Secondary expression of procollagen in tissues other than the mammary gland does not occur to an extent sufficient to cause deleterious effects. Moreover, virtually all exogenous procollagen produced in the mammary gland is secreted so that no significant problem is presented by deposits clogging the secretory apparatus.

The age at which transgenic mammals can begin producing milk, of course, varies with the nature of the animal. For transgenic bovines, the age is about two-and-a-half years naturally or six months with hormonal stimulation, whereas for transgenic mice the age is about 5–6 weeks. Of course, only the female members of a species are useful for producing milk. However, transgenic males are also of value for breeding female descendants. The sperm from transgenic males can be stored frozen for subsequent in vitro fertilization and generation of female offspring.

F. Cellular Expression Systems

The transgenes of the invention can also be transfected into mammary-gland derived cell lines (e.g., HC11 or MacT) to produce stable cell lines. These cell lines are capable of processing, assembling and secreting procollagen or collagen in trimeric form at high concentrations. Expression is induced by the synergistic effect of lactogenic hormones, such as insulin, hydrocortisone and prolactin, to the cell media.

G. Recovery of Proteins from Milk

Transgenic adult female mammals produce milk containing high concentrations of exogenous procollagen or collagen. Collagen or procollagen is purified from milk by virtue of its distinguishing physical and chemical properties. For example, acidification causes milk-specific proteins such as casein to precipitate while collagen or procollagen remains in solution. Collagen or procollagen is then precipitated by addition of salt, alcohol, or propylene glycol. See Miller & Rhodes, *Methods in Enzymology* 82, 33–63 (1982); Sage & Bernstein, id. at 96–127 (incorporated by reference in their entirety for all purposes).

H. Further Processing of Procollagen

The transgenic mammals of the invention usually secrete trimeric procollagen into milk without complete processing to the collagen form. Deferred processing is advantageous because substantial spontaneous processing to collagen might lead to formation of insoluble aggregates that block the mammary secretory pores. Conversion of procollagen to collagen can be completed by addition of proteases to the procollagen. The proteases are usually N and C-terminal procollagen proteases but nonspecific proteases (e.g., pepsin, trypsin, chymotrypsin, and papain) can also be used, in which case the telopeptide regions are also cleaved. In conventional use of bovine collagen for human therapy, cleavage of telopeptide regions has been found to render the collagen hypoantigenic. See Yarborough, *Am. J. Med. Sci.* 290, 28–31 (1985) (incorporated by reference in its entirety for all purposes). Cleavage reactions can be performed before or after purification of procollagen from milk. Following cleaving of propeptides and/or telopeptides, collagen spontaneously assembles into higher order insoluble fibrils suitable for reconstructive purposes. The remaining posttranslation modifications, that is lysyl oxidase conversion of some lysine and hydroxylysine residues to aldehyde derivatives that form interchain crosslinks, can be induced by supplying exogenous enzymes. Alternatively, crosslinks can be induced by a variety of chemical agents or ultraviolet irradiation (see, e.g., Simmons & Kearney, *Biotechnol. Appl. Biochem.* 17, 23–29 (1993) (incorporated by reference in its entirety for all purposes). Crosslinks can also be formed in situ, following injection into a patient. The extent of crosslinking introduced before injection varies depending on the therapeutic use to which collagen is to be put. See Chvapil et al., *Int. Rev. Connect. Tissue Res.* 6, 1–61 (1973) (incorporated by reference in its entirety for all purposes).

I. Uses of Collagen

The recombinant collagen and procollagen produced according to the invention find use in a wide variety of therapeutic procedures. Surgical procedures employing naturally occurring bovine collagen are already in extensive use. In general, the present recombinant collagens replace naturally occurring bovine collagen in these procedures. A common surgical procedure entails injected of collagen into a patient to correct defects in soft tissues, such as scars, traumatic and surgical defects and early wrinkles and creases. See Yarborough, supra. Another application is that of reconstructive surgery such as in the restoration of the tensile strength of tissues such as the sphincter of the bladder in the treatment of urinary incontinence. See Apprell et al., *Urologic Clinics of North America* 21, 177–182 (1994) (incorporated by reference in its entirety for all purposes). Collagens are also used in combination with ceramics and other materials to restore defects in bone and enhance bone growth. Type II collagens are particularly useful for the repair of cartilage damage. Collagen Type II can also be administered orally as a therapeutic agent for inducing tolerance to rheumatoid arthritis. The collagens of the invention are also employed in cardiovascular surgery, production of synthetic skin, ophthalmology, thoracic surgery, otology, neurosurgery, and as a stabilizing agent in drug delivery systems. The collagens are usually employed in high molecular weight fibrillar form. However, procollagens existing as individual trimeric units can also be used. In this case, processing to collagen and assembly of higher order forms takes place in situ after treatment of the patient. The methods are broadly applicable to human and veterinary subjects.

The following examples are provided to illustrate but not to limit the invention.

EXAMPLES

Example 1

Vectors for Collagen Expression a. PROα1(l) Collagen cDNA Based Expression Vector A plasmid vector was constructed containing the bovine αS1-casein 5'-flanking region including the proximal promoter operably linked to a cDNA sequence encoding the human proα(I) collagen gene, which is in turn operably linked to a 3'-flanking sequences derived from the human genomic collagen gene. The fusion product of the collagen tion. The two fragments were ligated resulting in the construct designated p8cCOL(A1)3. The structure of the construct was verified by NotI, EcoRI, NotI-SalI, ClaI/XbaI, HindIII, ClaI/SalI restriction mapping.

b. Constructionn of Vectors Based on the Human Genomic PROα1(I) Collagen Gene

The first intron of the human collagen (1) gene has been reported to contain both positive and negative transcriptional regulatory elements (Rossi et al., *Proc. Natl. Acad. Sci.* 84, 5590–5594 (1987)); Rossouw et al., *J. Biol. Chem.* 262, 15151–15157 (1987); Bornstein et al., *Proc. Natl. Acad. Sci.* 84, 8869–8873 (1987); Bornstein et al., *J. Biol. Chem.* 263, 1603–1606 (1988a); Bornstein et al., *Mol. Cell Biol.* 8, 4851–4857 (1988b) (incorporated by reference in their entirety for all purposes). Because the interaction of the enhancer-like elements of the first collagen intron with the casein 5'-flanking sequences used in the present studies was unpredictable, expression vectors were constructed with or without the first intron of the collagen gene. In both vectors, sequences from the 5'-end of the first exon of the collagen gene that form a predicted hairpin loop and probably inhibit translational efficiency of the collagen gene (Chu et al., supra, (1985)) were deleted. In both vectors, the predicted nucleotide sequence from the transcription start site (+1) to the initiation codon (underlined) of the collagen gene is:

cDNA [XbaISalI fragment] and the casein promoter at a ClaI site yields the following nucleotide sequence:

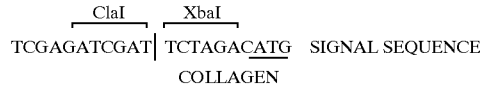

Figure 1B:
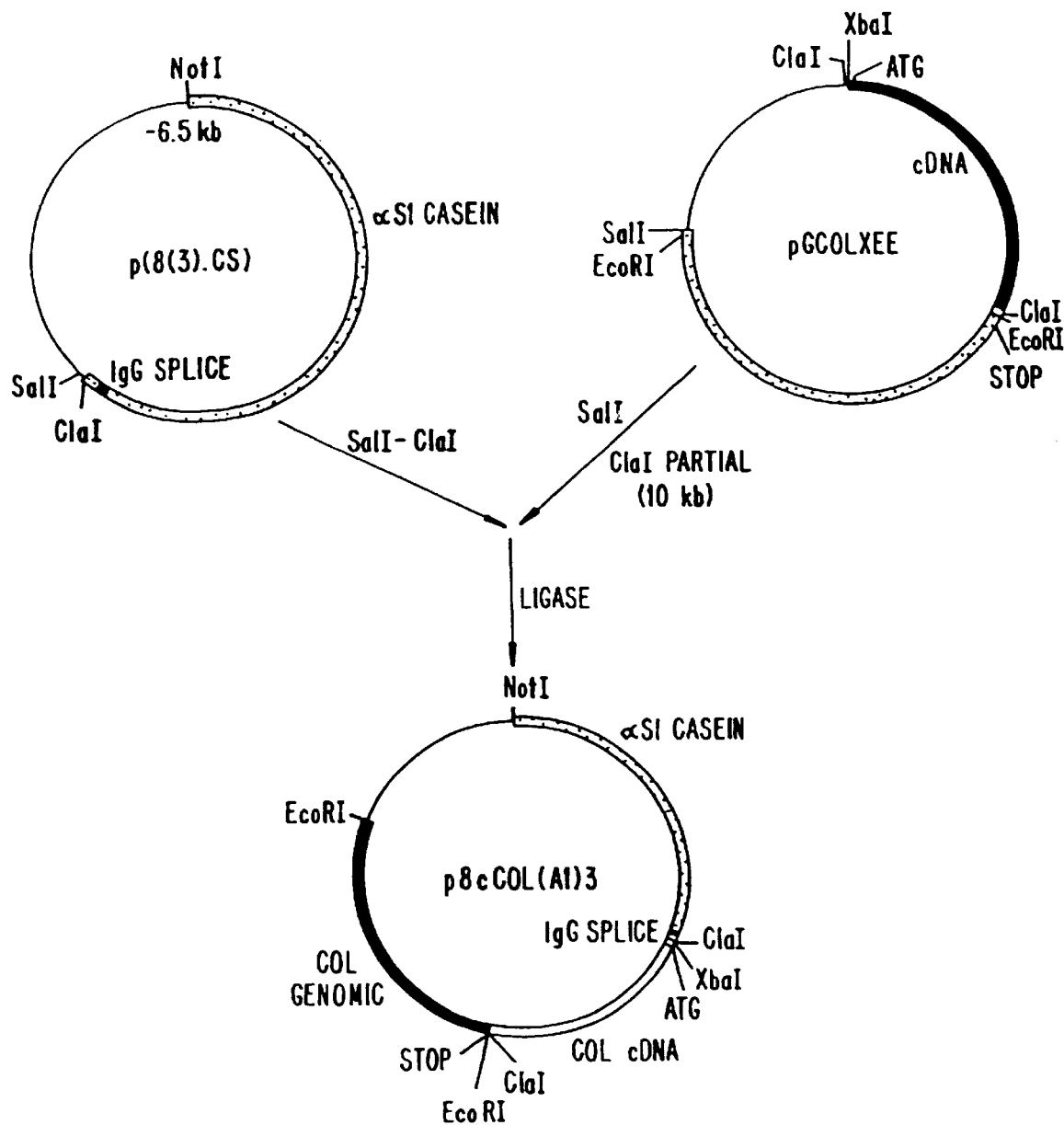

The XbaI-EcoRI fragment (4363 bp) of a collagen cDNA was subcloned into the XbaI-EcoRI site of pGEM-7B, giving rise to the pGCOLXE plasmid (FIG. 1). This collagen cDNA fragment lacks the region encoding for the last 10 amino acids of the protein. The full-length coding region of the human proα1(I) collagen was reconstituted by fusing a 5.7 kb EcoRI fragment (Schnieke et al., *Proc. Natl. Acad. Sci. USA* 84, 764–768 (1987)) derived from the GC103 genomic clone (FIG. 1) (Barsh et al., supra) to the EcoRI site of the pGCOLXE vector. This 5.7 kb fragment contains the nucleotides encoding for the last 10 amino acids of the collagen protein from exon 52, the stop codon, the collagen 3'-UTR and the 3'-flanking sequences including two polyadenylation sites at ~300 bp and 1314 bp downstream of the termination codon. The orientation of the subcloned fragment was confirmed by HindIII digestion and sequencing. The resulting plasmid pGCOLXEE is shown in FIG. 1.

The collagen sequences were placed under the control of the bovine αS1-casein promoter as follows. The plasmid [p(83), CS)] (FIG. 1), carrying a 6.2 kb αS1-casein promoter and fused to the human IgG splice acceptor site fragment (ca. 0.3 kb), was digested with SalI-ClaI. A 10 kb SalI-ClaI collagen fragment was excised from plasmid pGCOLXEE (FIG. 1) by SalI digestion followed by a partial ClaI diges- (1) Construct Containing the First Intron The strategy entailed linking an entire genomic clone of α1(I) procollagen (other than the 5' 114 bases which form the inhibitory hairpin loop) including about 20 kb of collagen 3' flanking sequence to a 5' αs1 casein flanking sequence including a promoter. The construct was assembled from four fragments.

Figure 2A:
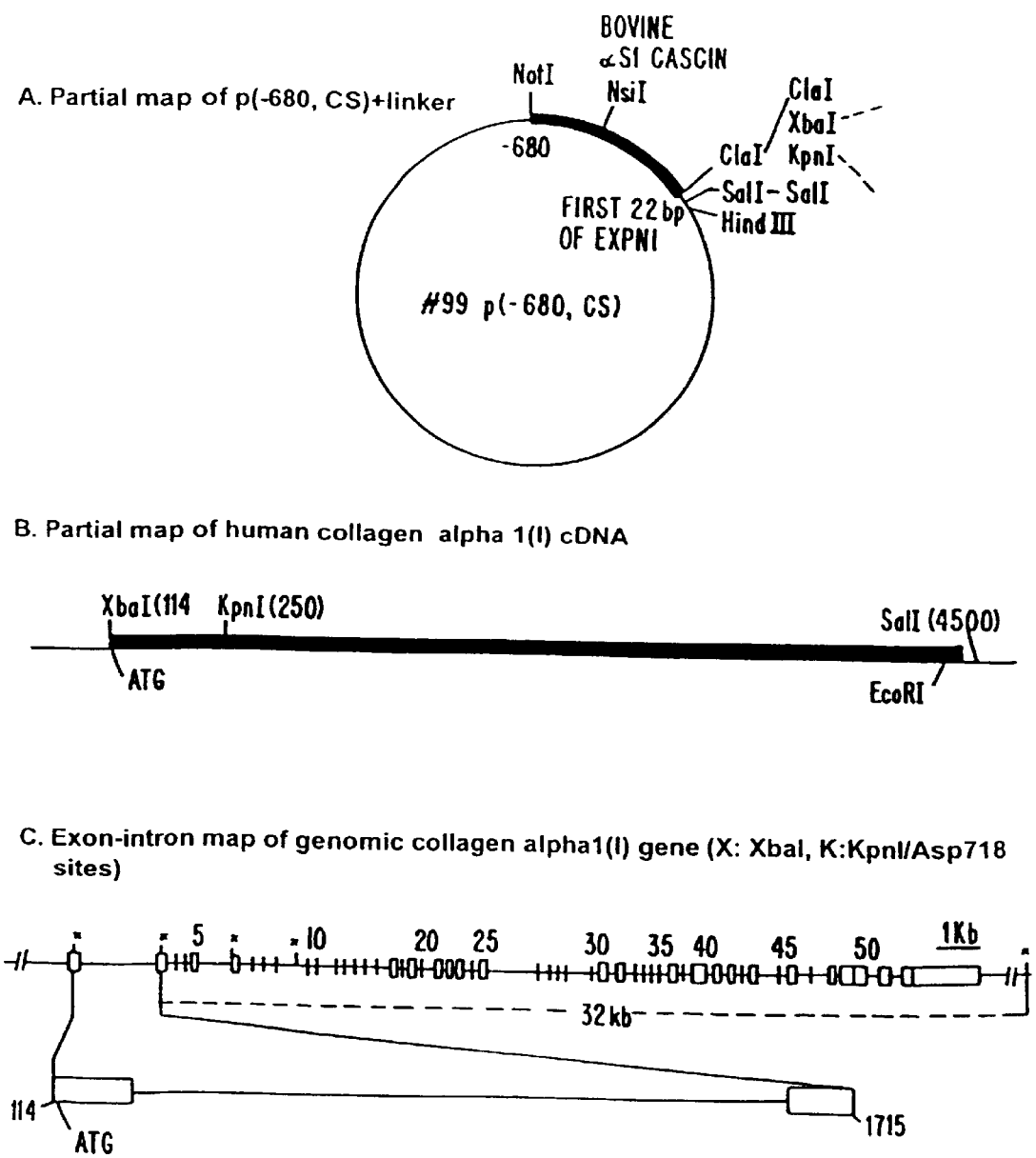
FIGS. 2(A–E): Construction of genomic transgenes for procollagen expression.
Figure 2B:
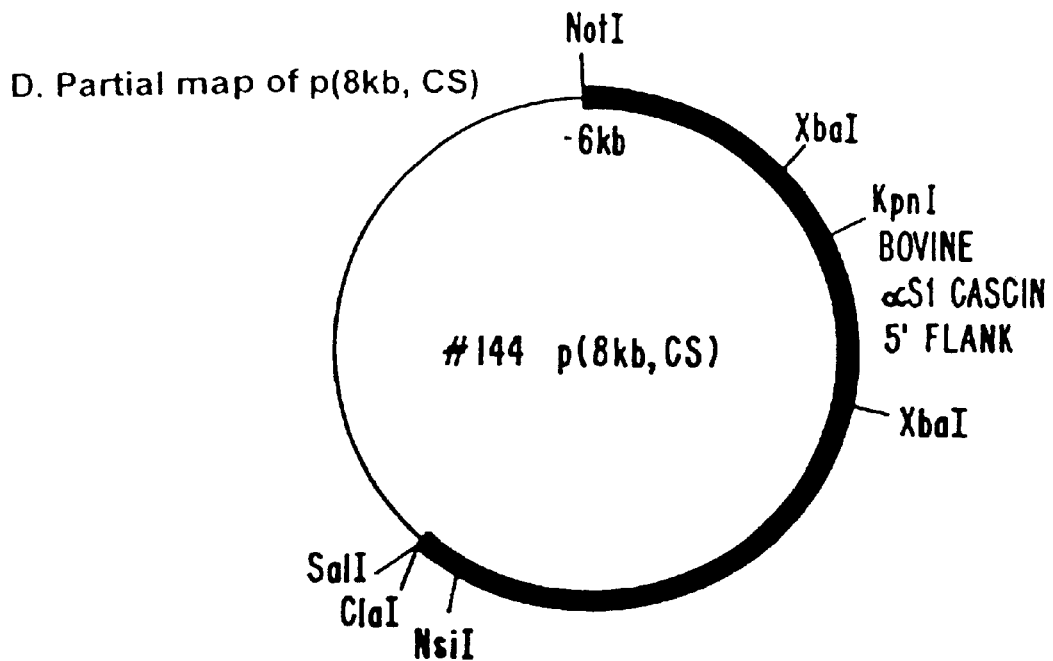
Figure 2B:
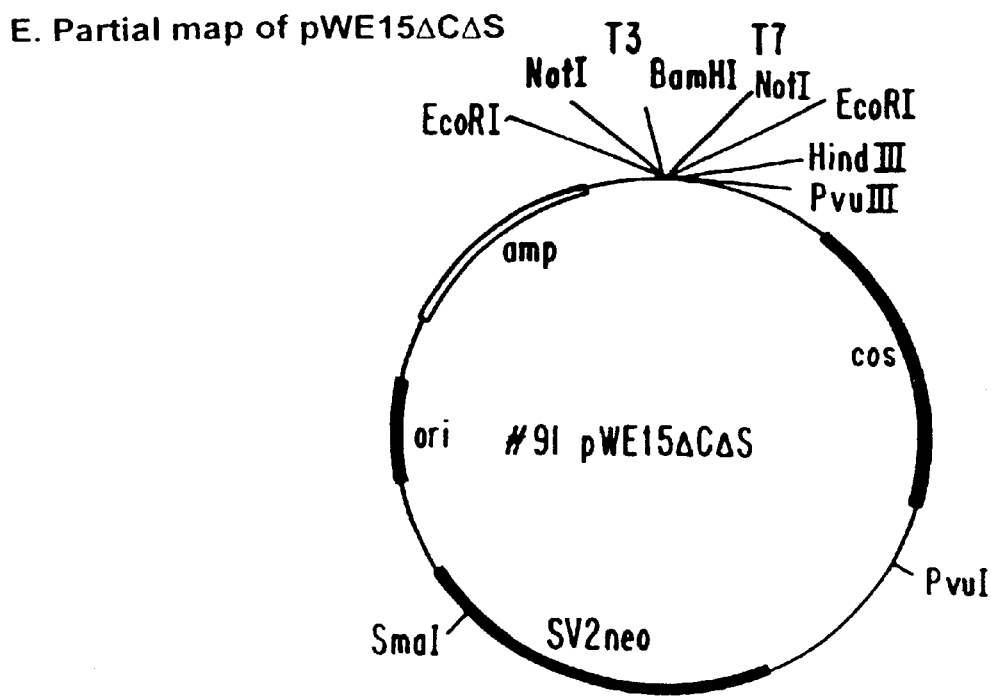

Plasmid p(-680,CS) which contains 0.7 kb of the αS1-casein promoter was modified by means of a ClaI-XbaI-KpnI-SalI linker introduced into the ClaI-SalI sites (FIG. 2, panel A) and verified by sequencing and restriction mapping. The plasmid was digested with XbaI-KpnI(Asp718) and ligated to a 1600 bp XbaI-KpnI fragment (positions 114 bp of the 1st exon to position 1715 bp of the second exon of the collagen GC103 genomic clone; FIG. 2, panel C). This cloning strategy resulted in pCOL1600. To fuse the 0.7 kb αS1-casein promoter to the additional 5' αs1 flanking sequences, PCOL1600 was digested with NotI-NsiI and purified. A 6.0 kb fragment of the αS1-casein promoter was excised from the p(8 kb, CS) plasmid (FIG. 2, panel D) by NotI-NsiI digestion and ligated to the pCOL1600 fragment. The resulting construct was designated p8COL1600. Construction of p8COL1600 was verified by NsiI-NotI, NsiI, Asp718, NotI-Asp718, XbaI and HindIII digestion. The casein promoter-collagen fusion fragments was released from p8COL1600 by NotI-partial KpnI(Asp718) digestion, resulting in an 8.1 kb DNA fragment containing αs1 5' flanking sequence and a 5' fragment from the α1 collagen gene.

The remainder of the α1 procollagen gene and 3' flanking sequence was cloned as a 32 kb Asp718-NotI fragment. PWE15ΔCΔS was digested with NotI (FIG. 2, panel E) and the linker NotI*-KpnI-SacII-SnaBI SunI-NotI was inserted (* indicates that this site is destroyed upon ligation). The resulting vector (pWESun) was digested with Asp718-SunI and a 32 kb Asp718-Asp718 fragment from collagen GC103 clone (FIG. 2, panel C) was ligated into these sites. The SunI site is compatible with Asp718 but it is not regenerated upon ligation. The 32 kb Asp718 genomic collagen fragment contains most of the collagen gene (from nucleotide 1716 of exon 2) plus approximately 20 kb of 3'-end (cosmid CG103). After packaging and transformation the orientation of the inserted fragment was confirmed by NotI-XhoI mapping.

The Asp718-NotI collagen fragment was excised, purified and ligated with the NotI/KpnI 8.1 kb fragment and with NotI digested, dephosphorylated pWE15ΔCΔS cosmid vector (FIG. 2, panel E) in a three-fragment ligation reaction. This ligation resulted in vector c8gCOL(A1), which contains the genomic collagen sequences (starting at position 114 of exon 1, i.e., 4 bp upstream from the initiation codon of translation) of clone GC103 (D'Alessio et al., Gene 67, 10–115 (1988). The structure of the construct was verified by EcoRI, XhoI-Asp718, HindIII and BamHI-NotI restriction analysis.

(2) Genomic Construct Lacking First Intron

This vector was constructed by the same strategy as described above except that a 147 bp XbaI-KpnI fragment (positions 114 bp-260 bp of the collagen cDNA; FIG. 2, panel B) was used instead of the 1600 bp XbaI-KpnI fragment. The equivalent to p8COL1600 in the previous method was designated p8COL150. A DNA segment containing the αs1 casein promoter and 5' procollagen sequence was excised from this vector as a 6.65 kb fragment. This fragment was ligated to the 32 kb Asp718-NotI genomic collagen fragment to yield the vector, c8gΔiCOL(A1). This vector is identical to c8giCOL(A1) except for the deletion of the 1454 bp first intron in the former.

C. Genomic Constructs Encoding Human α2(I) Procollagen

Three candidate clones for the human α2(I) procollagen gene were isolated from a P1 phage library from Genome Systems, Inc. (St. Louis, Mo.). The clones were probed with oligonucleotides from intron 1 and the 3' untranslated regions of the human α2(I) procollagen sequence described by de Wet et al., J. Biol. Chem. 262, 16032–16036 (1987) (incorporated by reference in its entirety for all purposes). One of these clones contained the full-length gene. Analysis of the human α2(I) procollagen gene sequence in the Genbank/EMBL database identified a Cel2 restriction site within exon 1 which overlaps the translation start site (see FIG. 7, panel A). This Cel2 site provides a convenient site for fusion of the human α2(I) procollagen gene with the bovine αS$_1$-casein 5' untranslated sequence. Mapping of this site within a 5' XhoI/BamHI fragment showed the presence of a second Cel2 site approximately 2 kb downstream of the translation start site. See FIG. 7 (panel A).

The genomic clone was reconstructed in the vector pWE15 by one of two strategies. In a first strategy, a synthetic polylinker containing convenient restriction sites was inserted into the cosmid vector pWE15 at the EcoRI/NheI site. The restriction sites within the polylinker (designated oligo A) are shown in FIG. 7 (panel B). The 5' XhoI/BamHI fragment of the human α2(I) procollagen gene was then introduced into the XhoI/BamHI site of the cosmid vector. The XhoI site is approximately 500–1000 bp upstream of the transcription start site. The endogenous 5' untranslated region of the α2(I) procollagen gene between sites XhoI and Cel2 was replaced with the bovine casein 5' untranslated region (designed oligo B).

<u>ATCGATTTGCTTCTTTCCAGTCTTTCTAGA</u><u>CAT</u>
　ClaI　　　　　　　　　　　　　　　　Met

The orientation of the Cel2/Cel2 fragment following these manipulations was determined by DNA sequencing. Finally, the remainder of the human α2(I) procollagen gene (a 29 kb BamHI/BamHI fragment) was inserted at the BamHI site linked to the modified 5' end of the gene. The orientation of the BamHI/BamHI fragment was checked by restriction mapping. The reconstructed gene (FIG. 7, panel C) was then linked to the bovine αs1-casein promoter-enhancer fragment as described above for the α1(I) procollagen gene.

The second strategy used the same initial steps as the first strategy, but instead of ligating the 29 kb BamHI-BamHI α2(I) procollagen fragment ligated two fragments, a XhoI-BamHI fragment containing the α2(I) procollagen and a XhoI-XhoI fragment containing the α2(I) procollagen 3' end. The resulting construct has a 4 kb longer 3' flanking sequence than the construct produced by the first strategy (5.5 kb vs. 1.5 kb) (FIG. 7, panel C). The construct otherwise contains the same restriction sites as the gene construct from the first strategy with which to link it to the bovine αS$_1$-casein promoter-enhancer fragment.

Example 2

Expression of Constructs in Mammary Cell Culture

This example shows the feasibility of expressing, assembling and secreting an α1(I) procollagen in mammary gland cells, a cell type that does not normally express this gene. The cDNA and genomic vectors described above were transfected in their circular form into the mouse mammary epithelial cell line HC11 (Ball et al., EMBO 7, 2089–2095 (1988)). The cells were maintained as monolayers in RPMI 1640 (10% FCS, 2mM L-Glutamine, 50 g/ml gentamicin, 5 μg/ml insulin, 10 ng/ml EGF). 30–40 μg of each construct together and a hygromycin-resistance cotransfecting plasmid were complexed with 50 μg lipofectine (Gibco) and allowed to fuse with 2–3×10$^6$ cells. After 48 hr of growth in normal medium, selection medium was applied to select for stable transfectants. Two independent transfection rounds have been performed, and resistant colonies were scored after about 2 weeks (Table 1).

TABLE 1

TRANSFECTION OF COLLAGEN EXPRESSION VECTORS

| CONSTRUCT: | NUMBER OF COLONIES: | |
|---|---|---|
| | TRANSF. 1: | TRANSF. 2: |
| p8cCOL(A1)3 | 900 | 800 |
| c8gCOL(A1) | 45 | 500 |
| c8gΔiCOL(A1) | 30 | 150 |

Colonies derived from independent transfection experiments were pooled and 10$^6$ cells were seeded in 6-well plates and grown to confluence. Cells received either normal medium or medium containing lactogenic hormones. Some cells also received 50 μg/ml sodium ascorbate. RNA was harvested from cultures and analyzed for expression of human collagen.

a. Northern Blotting

Human α1(I) collagen mRNA was detected by Northern blotting. Total RNA was isolated from tissues and cells grown under different conditions by the RNAzol method (Tell-test). 10–20 μg of total RNA was separated on 1.0% agarose formaldehyde gels (Sambrook et al., *Molecular Cloning: A Laboratory Manual* (2d ed.) CSHP, CSH, NY (1989)) (incorporated by reference in its entirety for all purposes) and transferred to Hybond filters (Amersham). The 4.3 kbp XbaI-EcoRI fragment isolated from the hCOL cDNA clone was used as a probe.

Figure 3A:
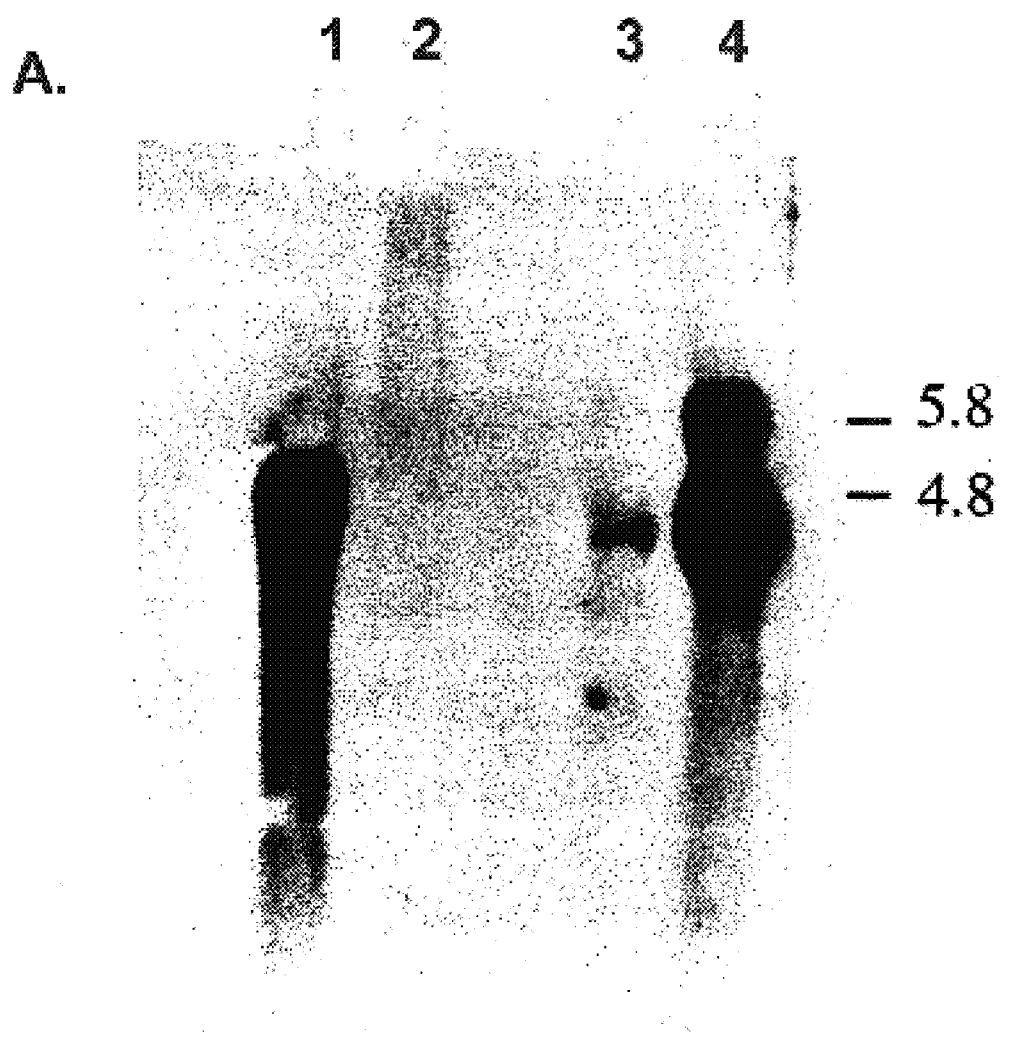
FIGS. 3(A–B): Northern blot of mRNA in tissue and cell lines with (B) and without (A) transfected procollagen transgene.
Figure 3B:
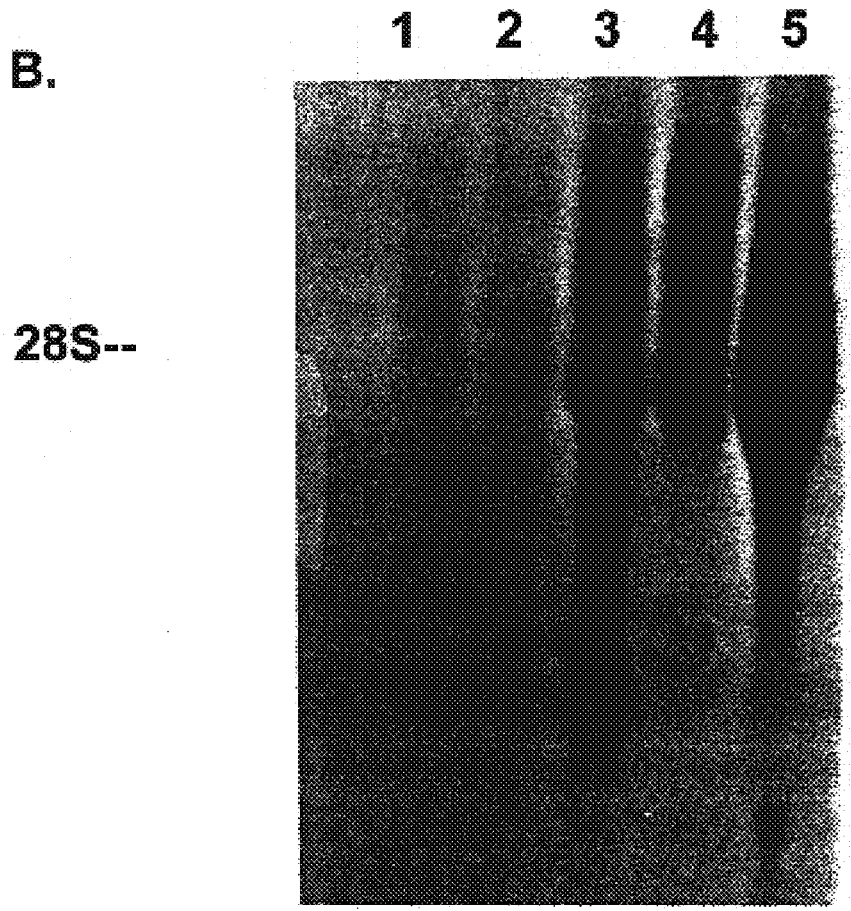
Figure 3B:
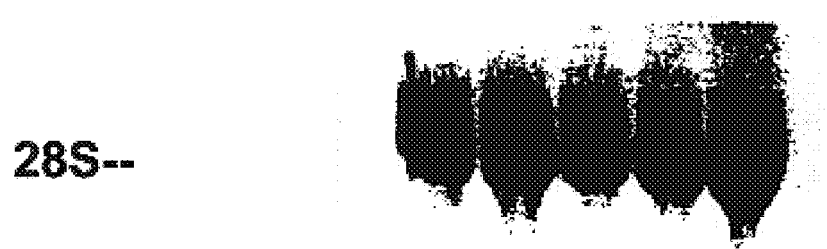

FIG. 3 (panel A) shows RNA obtained from mouse fibroblast cells (3T3, lane 1) (expected to express collagen type I), mouse mammary gland (lactating day 8, lane 2) (not expected to express collagen), human keratinocytes (lane 3) (expected to express collagen), and human fibroblasts (lane 4) (expected to express collagen). The latter two lanes showed the two expected 4.8 kb and 5.8 kb collagen transcripts. The mouse fibroblasts (3T3) sample cross-hybridized with the human probe resulting in a 4.8 kb band. The lactating mammary gland samples (consisting mainly of epithelial cells) did not show any cross-hybridizing band.

FIG. 3 (panel B) shows RNA from control HC11 cells and HC11 cells transfected with the above vectors after culturing cells in complete medium. The control cells in lanes 1 and 2 do not cross hybridize with the human collagen probe. Lanes 3, 4, and 5 containing RNA from cells transfected with c8gΔiCOL(A1), p8cCOL(A1)3, and c8gCOL(A1), respectively, show a 4.8 kb transcript. The presence of the transcript shows that all 3 collagen expression vectors are transcribed and produce human collagen mRNA.

b. Immunofluorescence Staining

Transfected cells were seeded in 8-well chamber slides and grown to confluency. Normal medium or medium containing lactogenic hormones was added to the cells. Some cells also received 50 μg/ml sodium ascorbate. After culturing, the cells were fixed (cold acetone/methanol (1/1) for 10 min, −20° C.), and incubated with a 1:400 dilution of a rabbit polyclonal antibody specific for the C-terminus of type I human pro α1(I) (Collagen Corp., Palo Alto, Calif.). After thorough washing, anti-rabbit IgG FITC-conjugate (Sigma, 1:200 dilution) was added. The detection of human collagen was performed by fluorescence microscopy, and representative sections of the slides were photographed.

Figure 4:
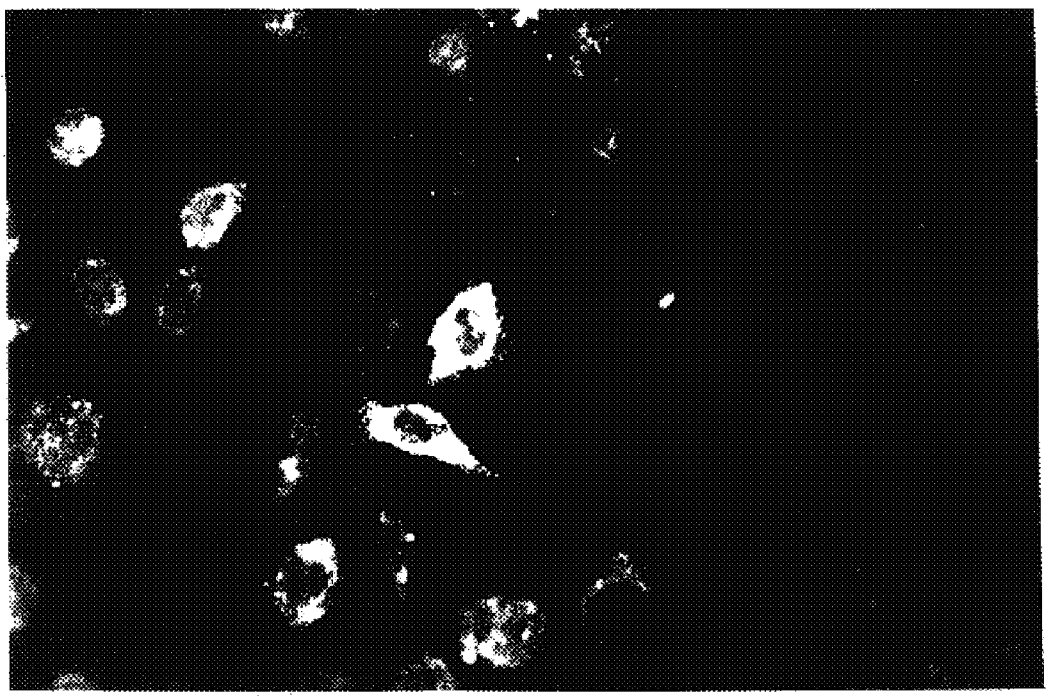
FIGS. 4(A–B): Immunofluorescence staining of mammary gland cell lines transfected with genomic transgenes for procollagen expression.
Figure 4:
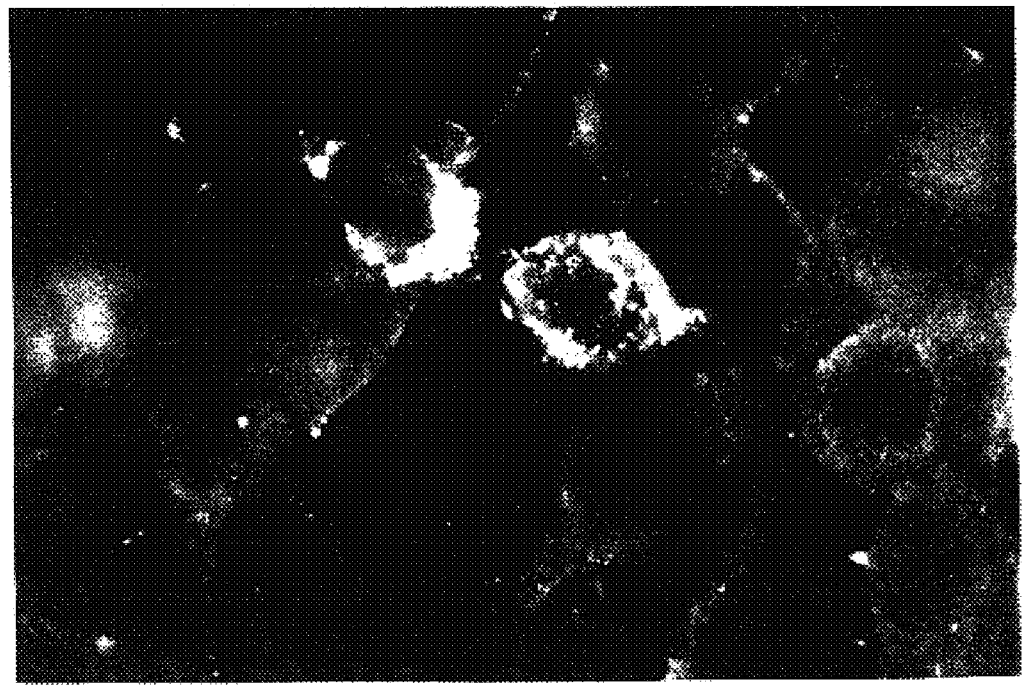

FIG. 4, panel A shows cells transfected with construct c8gCOL (A1) and panel B shows cells transfected with construct c8gΔiCOL(A1). In the transfected cell pools, strongly stained cells were observed displaying a typical intracellular-patchy-granular staining pattern. The results indicate that cells within the pools express the transgene. The cells appear to express the human collagen at variable levels perhaps reflecting their different chromosomal sites resulting from random integration. Control HC11 cells showed background staining but with a different distribution of signal surrounding the cell surface.

c. Protein Analysis

Medium and cytoplasmic extracts from control HC11 cells (murine) and MacT cells (bovine) (Huynh et al., *Exp. Cell Res.* 197, 191–199 (1991)), as well as from the HC11 cells transfected with the above vectors were prepared as follows. About 2×10$^7$ cells were plated in medium (HC11 cells in RPMI 1640; MacT cells in DMEM supplemented with 10% FCS, 2 mM L-Glutamine, 50 μg/ml gentamicin, 5 μg/ml insulin, 10 ng/ml EGF) with or without 50 μg/ml sodium ascorbate. The cells were cultured for 24 hours. The medium was then harvested in the presence of protease inhibitors (PMSF, EDTA, leupeptin, and pepstatin), and lyophilized. The cells were lysed in lysis buffer (50 mM Tris pH 8, 150 mM NaCl, 0.1% SDS, 1% NP40 supplemented with the protease inhibitors). The cytoplasmic fraction was then harvested and lyophilized. The medium and cytoplasmic samples (as well as negative mouse milk samples) are analyzed for the presence of human α1(I) protein by ELISA and Western blotting.

Example 3

Production of Transgenic Animals Expressing α1(I) Procollagen (1) Transgenesis

Collagen transgene fragments were excised from the three vectors described in Example 1 by NotI digestion and purified by 0.65% agarose gel electrophoresis and electro-elution. (FIG. 2, panel A). Fertilized mouse eggs (CBA/BrAxC57B1/6) were microinjected (with 100–200 copies of the fragment) and transferred into pseudo-pregnant females as described (Hogan et al., supra). Total genomic DNA was prepared from a short segment of mouse tail to check for integration of the injected DNA. EcoRI-digested tail DNA was analyzed by Southern blotting (Sambrook et al., supra). The probe used to check for integration of the transgene was a 300 bp NcoI-NsiI fragment, spanning the region from −680 to −250 (relative to the major transcription start site) of the bovine αS1-casein gene. The probe was labeled with $^{32}$P using random hexanucleotide primers (Sambrook et al., supra). The numbers of transgenic mice containing one of the 3 vectors described in Example 1 are as follows:

c8cCOL(A1)3: 23 transfers have been performed and out of the 15 resulting pregnancies 59 pups were tested. From these, 4 were shown to be transgenic (3 male and 1 female).

c8gCOL(A1): 32 transfers have been performed and out of the 27 resulting pregnancies 108 pubs were tested. From these 13 were shown to be transgenic (8 males and 5 females).

c8gΔiCOL(A1): 34 transfers have been performed and out of the 27 resulting pregnancies 53 pups were tested. From these, 10 were shown to be transgenic (7 males and 3 females).

All transgenic mice were mated to obtain F1 offspring (both in case of males and females), and F0 milk (in case of females).

(2) Protein Analysis

Milk from lactating mice was collected 10 min after subcutaneous injection of 1 unit of oxytocin (PitonS, Organon) to induce milk secretion. Milk samples were supplemented with protease inhibitors (PMSF, EDTA, leupeptin, pepstatin), and frozen at −80° C. until analysis. 5 μl mouse milk (control and transgenic) was diluted tenfold in PBS. 5 μl samples were then analyzed by SDS PAGE under reducing (lanes 1–8) and nonreducing conditions (lanes 9–15).

Figure 5:
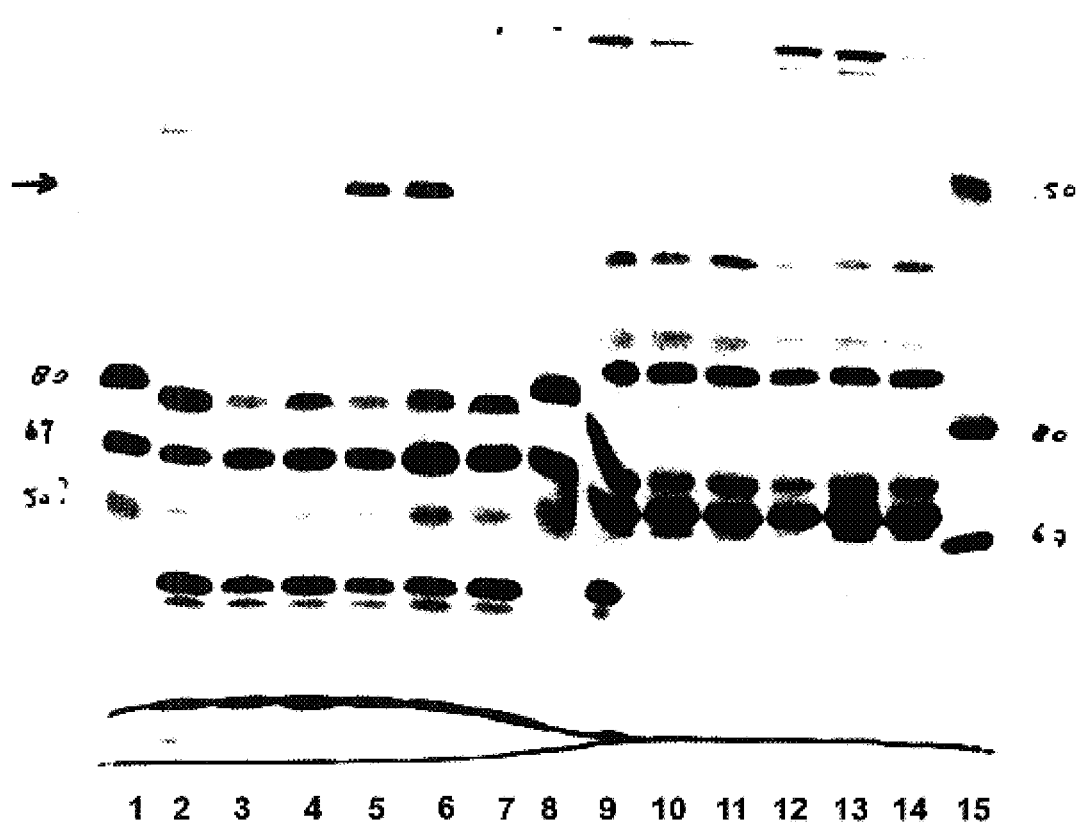
FIG. 5: SDS-PAGE analysis of milk from transgenic or control mice. Tracks 1–8 reducing conditions; tracks 9–15, nonreducing conditions. The lanes contain.

FIGS. 5 and 6 shows that milk from transgenic mice contain a band of about 160 kDa that was not present in the milk of control mice. The 160 kDa observed on the gels is close to the anticipated molecular weight for the monomeric form of α1(I) procollagen as measured by PAGE. Because secretion of procollagen is believed to be dependent on the prior posttranslational modifications and assembly into a trimeric structure, the observation that secretion has occurred indicates that prior modification and assembly have also occurred. Analysis of the same samples under nonreducing conditions indicated the presence of several higher molecular weight bands in the milk from transgenic mice that were not present in the controls. These bands are likely trimeric procollagen, trimeric collagen or higher order forms of collagen. The figure indicates that most, if not all of the procollagen in transgenic mouse milk was in the form of higher order structures. This result shows that the procollagen polypeptide chains are able efficiently to associate with each other within the mammary epithelium. Therefore, provision of an exogenous chaperon protein to express recombinant procollagen in mammary tissue is not necessary.

(3) Confirmation that ~160 kDa Band in Reducing Gels is Procollagen

Transgenic milk samples were analyzed by Western blotting. The antiserum was directed against the amino-terminus of human α(1) procollagen. A milk sample from founder 2395 was processed as described for SDS-PAGE and run under nonreducing conditions, followed by transfer to nitrocellulose filters. Signal was detected using the ECL system (Amersham). No signal was observed with negative mouse milk (FIG. 8, track 1). Therefore, the antibody does not crossreact with nontransgenic mouse milk. Track 2 contains milk from founder 2395. The proteins produced in the milk of founder 2395 do crossreact with the antibody. This indicates that the proteins are procollagen, collagen or higher forms thereof, and that the antigenic determinants are similar to those in the native procollagen protein.

Further confirmation that the new polypeptide chain found in the milk of some transgenic mice is the expression product of the human α(1) procollagen gene introduced into these mice was obtained by digesting milk samples with collagenase. Milk from mouse 2395 was treated with bacterial collagenase followed by electrophoresis through a 5% polyacrylamide gel. The procollagen band at about 160 kDa disappeared (see FIG. 9).

(4) Concentration of Procollagen

The concentration of type I procollagen in milk samples was determined by the Prolagen-C kit (Metra Biosystems, Palo Alto, Calif.). The kit reports the values in ng/μl of carboxy-propeptide; therefore, the concentration of HSF samples were corrected by a factor of 4.5 to account for the entire procollagen molecule. 0.5 μl of mouse milk was denatured and electrophoresed on an SDS page gel in comparison with collagen standards of known concentration. Concentrations were determined by comparison of band intensities. Concentrations of procollagen from mice harboring a cDNA construct were too low to detect. Concentrations from mice harboring a genomic construct were in the range of 4–10 mg/ml.

A summary of the expression levels is listed in Table 2. In four mouse lines in which expression was examined for both the founder and her F1 offspring, the relative expression levels were comparable.

TABLE 2

Expression Levels of Transgenic Mice containing the Human α1 (I) Procollagen DNA

| | Relative expression level | | | |
|---|---|---|---|---|
| construct | none | low | med. | high |
| p8cCOL(A1)3 | 3 | 1 | 0 | 0 |
| c8gCOL(A1) | 3 | 3 | 3 | 1 |
| c8gΔiCOL(A1) | 2 | 2 | 3 | 1 |

High level expression indicates greater than about 4 mg/ml, medium expression indicates about 0.8–4 mg/ml and low expression about 0.1–0.8 mg/ml. Constructs indicated as nonexpressors may express at lower levels detectable by Western blotting. The numbers represent independent transgenic female founder mice and/or transgenic mouse lines. All F1 mice carrying more that one intact copy of a genomic transgene expressed in the mg/ml range.

(5) Proteolytic Digestion Analyses

The structural integrity of procollagen from milk of transgenic mice can be tested by digestion with proteases. The ends of natural procollagen molecules are susceptible to digestion by proteases, whereas the central trimeric region is resistances. Milk samples from transgenic mice were prepared for digestion by the method of Bruckner & Prockop, Annal. Biochem. 110, 360–368 (1981). Samples were diluted into 10 mM Tris, 0.1 mM EDTA, 150 mM NaCl, pH 7.4, and digested with a mixture of trypsin/chymotrypsin (in 4- and 40-fold molar excess respectively) for 1 hour at 20° C. The reaction was terminated by the addition of soybean trypsin inhibitor. The samples were heated to 65° C. for 20 min and run on a 7.5% SDS-polyacrylamide gel and stained with Coomassie R-250.

FIG. 10 (Panels A and B) shows that digestion of two positive controls (i.e., media samples from cell lines which produce human type I procollagen heterotrimer and homotrimer) produces the expected reduction of size upon enzymatic digestion from procollagen to collagen retaining only the triple helical region [i.e., from about 160 kDa to about 100 kDa). A second band migrating faster than collagen also appears which corresponds to an intermediate degradation product. Two samples of milk from transgenic mice (one each from the genomic constructs c8gCOL(A1) and c8gΔiCOL(A1) also showed this pattern, although the intermediate degradation product was more pronounced (FIG. 10, panels C and D). The similarity of profiles between the milk samples and the procollagen controls shows that the type I procollagen polypeptides in milk are, like the controls, assembled into a triple helix.

To test the stability of the trimeric form of procollagen produced by transgenic mice, a temperature profile of the procollagen molecule was obtained by increasing reaction temperatures of the trypsin/chymotrypsin digestion. The results are shown in FIG. 10. The melting temperature, or Tm, was defined as the temperature at which one-half of the bands corresponding to collagen and distinct degradation intermediates were digested by trypsin/chymotrypsin. FIG. 10 indicates that the thermal stability of trimeric collagen from transgenic mice is about 30° C. Although these data evidence a substantial stability, the stability is somewhat lower than of native type I collagen (40° C.) or homotrimic collagen produced in cell culture (38° C., as reported by Geddis & Prockop, Matrix 13, 399–405 (1993). The difference in melting temperatures is likely the result a lower degree of hydroxylation of proline residues in procollagen from the transgenic mice.

Stability of trimeric collagen produced by transgenic mice was also tested by pepsin digestion. Like trypsin and chymotrypsin, pepsin cleaves within the Gly-X-Y region of denatured procollagen, but is unable to cleave when the procollagen polypeptides are in a triple helical conformation. A pepsin digestion was performed on type I procollagen hetero- and homotrimers (as controls) and on mouse milk samples from mice 2395 and 2399 using conditions optimized for complete digestion of denatured procollagen. The digestion by pepsin was for 2 h at pH 2.5. The samples were neutralized with 1 M Tris and then loaded onto a 5% SDS-PAGE gel. The Tm for both the heterotrimeric and homotrimeric procollagen controls is approximately 40° C. and the procollagen molecules isolated from these two cell lines melt over a narrow temperature range. The procollagen in milk from mouse lines 2395 and 2399 has a Tm of about 30° C. and 32.5° C., respectively. Thus, procollagen in the milk from mouse 2399 appears to be slightly more resistant to thermal denaturation than the procollagen in the milk from mouse 2395.

(6) Amino Acid Composition

This experiment determines the amino acid composition of the human α1(I) procollagen in the milk of transgenic mice. Milk from lines previously determined to be relatively high expressors (mg/ml range) along with control collagen samples (HSV and SV), were isolated from 5% SDS PAGE gels. The gel was cut to isolate the procollagen bands. Each of the gel slices was incubated at 4° C. overnight to elute the protein from the gel slice (Fleick & Shiozawa, Analyt. Biochem. 187, 205 (1990). The supernatant was recovered after centrifugation and lyophilized. The protein samples were dissolved and reprecipitated (Wissel & Flugge, Analyt. Biochem. 138, 141–143 (1984)). 1.5–4 μg was recovered for each sample, except for 2465, for which 0.75 μg was recovered. HSF and SV samples were run in duplicate. Amino acid analysis of the samples was performed under conditions which would quantify hydroxyproline residues. Under these conditions, both aspartic acid and asparagine comigrate and glutamic acid and glutamine comigrate (due to the loss of amino group of Asn and Gln, respectively, during processing). Approximately 90% of serine and threonine were recovered. Cysteine and methionine can be partially or fully oxidized under these conditions, so their values may have been lower than expected. Tryptophan was completely destroyed under these conditions and therefore was undetectable. Glycine content was high due to some carryover from the buffer within the acrylamide gel. Both hydroxy-proline (HyP) and hydroxy-lysine (HyL) were quantified.

TAbLE 3

Measurement of Hydroxylated Amino Acids

| sample | OH-Pro (Pro + OH-Pro | OH-Lys (Lys + OH-Lys) |
|---|---|---|
| HSV | 45% | 43% |
| SV | 47% | 54% |
| 2395 | 13% | 2% |
| 2410 | 7% | 0% |
| 2399 | 27% | 5% |
| 2402 | 19% | 2% |
| 2409 | 11% | 4% |
| 2465 | 7% | 0% |

Table 3 shows about equal amounts of proline and hydroxyproline (45% and 47%) for HSF and SV control samples, respectively, in agreement with prior measurements (Steinmann et al., J. Biol. Chem. 259, 11129–11138 (1984). Substantial levels of hydroxyproline (from 7% to 27%) were also detected in all procollagen samples isolated from the milk of transgenic mice. Therefore, proline residues in procollagen from transgenic mice were hydroxylated at levels of about 15–60% of the controls. Higher levels of hydroxylation can be induced, if desired, by altering the feed of the animals, introducing an additional transgene expressing prolyl hydroxylase or optimizing expression levels. Expression can be lowered to optimal levels by using a less efficient enhancer-promoter fragment, or using cDNA or cDNA-genomic hybrid constructs.

Levels of lysine hydroxylation were much lower in the procollagen isolated from milk of transgenic animals relative to procollagen from control samples. The low levels of hydroxylation offer the advantage of reducing aggregation of procollagen into higher order structures in milk, facilitating handling. Formation of higher order structures can be induced in vitro or can proceed in situ after injecting procollagen into a patient.

(7) Histology of Mammary Glands

Mammary glands from several transgenic mice were fixed in 10% formalin in preparation for histological analysis. The samples included glands from negative mice, a nonexpressing cDNA-containing transgenic mouse (line 2392), and three medium to high-expressing lines of transgenic mice (lines 2395, 2399, 2410, 2412). There were no significant differences between normal and transgenic mice.

(8) Tissue-Specificity of Expression

RNA was extracted from the mammary glands of transgenic mice and control nontransgenic mice and analyzed by Northern blotting as described above. The probe was a 23 bp oligonucleotide specifically hybridizing to the 5' casein UTR of the transgene. Samples from transgenic mice harboring either of the genomic α1(I) constructs showed two labelled bands of the expected length for transgene-specific transcripts (4.8 and 5.8 kb). Samples from nontransgenic mice did not give rise to transgene-derived transcripts.

RNA was also analyzed from various tissues of transgenic mice to investigate the tissue specificity of transgene expression. The mouse selected for this analysis was mouse 2817 (line 2395). This mouse line displays the highest level (>10 mg/ml) of procollagen. Northern blots of RNA from the mammary gland, brain, lung, thymus, kidney, liver, salivary gland, tongue, muscle leg, muscle belly, heart intestine, ovary and stomach are shown in tracks 2–17 of FIG. 11. Track 1 contains RNA from the mammary gland of a nontransgenic mouse. Only track 2 (mammary gland of transgenic mouse) shows bands of the expected size representing transgene-derived transcript. It is concluded that in mouse 2817 (the highest expressor to date), the transgene is expressed solely in the lactating mammary gland.

As will be clear to those skilled in the art from the above, the invention includes a number of general concepts which can be expressed as follows.

Thus, one general aspect of the invention is the use of a transgenic non-human mammal in the expression of an exogenous procollagen or collagen, said expression being mammary gland-specific expression of a transgene which includes a recombinant DNA segment encoding an exogenous procollagen polypeptide.

In another aspect, the invention includes the use of a DNA segment encoding a human procollagen polypeptide in the production of a transgene for the mammary gland-specific expression of an exogenous procollagen or collagen in a transgenic non-human mammal.

Yet a further aspect of the invention is the use of a DNA segment encoding an exogenous procollagen polypeptide in the production of a stable non-human mammary gland cell line, which cell line incorporates a transgene and has the ability when induced by a lactogenic hormone to express the transgene to produce exogenous procollagen or collagen.

In the first of the above-mentioned uses, a second transgene may be provided which includes a recombinant DNA segment encoding a prolyl hydroxylase enzyme such that, in the adult form of the non-human mammal or a female descendant thereof, said second transgene is capable of being expressed in the endoplasmic reticulum of the mammary secretory cells to produce the prolyl hydroxylase enzyme in an amount sufficient to hydroxylate the exogenous procollagen polypeptide such that the polypeptide is assembled and secreted in the trimeric form.

In another preferred aspect of the first of the above-mentioned uses, a second transgene may also be employed such that, in the adult form of the non-human mammal or a female descendant thereof, the first and second transgenes are capable of expressing respective first and second recombinant DNA segments therein in the mammary secretory cells of said animal to produce forms of α1(I) and α2(I) procollagen that are processed and secreted by said mammary secretory cells into milk as a trimer comprising at least one chain of α1(I) procollagen or collagen and at least one chain of α2(I) procollagen or collagen.

In all of the above uses, a further aspect may be the inclusion of a mammary gland specific enhancer and a mammary gland specific promoter.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A transgenic nonhuman mammal having a transgene comprising:
   a mammary-gland specific promoter;
   a mammary-gland specific enhancer
   a secretory DNA segment encoding a signal peptide functional in mammary secretory cells of the transgenic nonhuman mammal; and
   a recombinant DNA segment encoding an exogenous procollagen polypeptide operably linked to the secretory DNA segment to form a secretory-recombinant DNA segment, the secretory-recombinant DNA segment being operably linked to the promoter and to the enhancer;
   wherein the transgene, in an adult form of the nonhuman mammal or a female descendant of the nonhuman mammal, expresses the secretory-recombinant DNA segment in the mammary secretory cells to produce a form of the exogenous procollagen polypeptide that is processed and secreted by the mammary secretory cells into milk as exogenous procollagen or collagen in a detectable amount;

provided the recombinant DNA segment comprises a genomic DNA segment from the α1(I) collagen gene and is without nucleotides 1–114 from the first exon of the gene, and/or without a segment from the first intron of the gene.

2. The transgenic nonhuman mammal of claim 1, wherein the exogenous procollagen or collagen is in trineric form.

3. The transgenic nonhuman mammal of claim 2, wherein the transgene comprises:

a casein promoter;

a casein enhancer; and a genomic DNA segment comprising a segment from a signal peptide coding sequence to a 3' flanking region of a procollagen α1(I) or α2(I) gene, operably linked to the promoter and the enhancer and the concentration of the exogenous collagen or collagen in the milk is at least 100 μg/ml.

4. The transgenic nonhuman mammal of claim 3, wherein the genomic segment further comprises a 5' untranslated region from the procollagen α1(I) or α2(I) gene.

5. The transgenic nonhuman mammal of claim 3, wherein the genomic DNA segment is from the α1(I) gene and is without nucleotides 1–114 from the first exon of the gene.

6. The transgenic nonhuman mammal of claim 5, wherein the genomic DNA segment is without a segment from the first intron of the gene.

7. The transgenic nonhuman mammal of claim 3, wherein the concentration of the exogenous collagen or collagen in the milk is at least 1 mg/ml.

8. The nonhuman transgenic mammal of claim 7, wherein the exogenous procollagen or collagen polypeptide is human.

9. The nonhuman transgenic mammal of claim 8, wherein the exogenous procollagen or collagen polypeptide is proα1(I).

10. The nonhuman transgenic mammal of claim 1, wherein the recombinant DNA segment is a cDNA-genomic DNA hybrid.

11. The nonhuman mammal of claim 1, wherein the genomic segment comprises a contiguous segment from the 5' untranslated region to the 3' untranslated region of a human proα1(I) gene.

12. The nonhuman transgenic mammal of claim 1, wherein the genomic segment lacks a segment from the first intron of a human proα1(I) gene.

13. The nonhuman transgenic mammal of claim 1, wherein the first transgene encodes α1(I) procollagen and the nonhuman transgenic mammal has a second transgene comprising:

a second mammary-gland specific promoter, the same or different from the mammary-gland specific promoter;

a second mammary-gland specific enhancer, the same or different from the mammary-gland specific enhancer;

a second secretory DNA segment encoding a signal peptide functional in mammary secretory cells of the transgenic nonhuman mammal, the same or different from the secretory DNA segment; and a second recombinant DNA segment comprising a genomic DNA segment comprising a segment from a signal peptide coding sequence to a 3' flanking region of a procollagen α2(I) gene, operably linked to the promoter and the enhancer encoding a human α2(I) procollagen polypeptide operably linked to the second secretory DNA segment to form a second secretory-recombinant DNA segment, said secretory-recombinant DNA segment being operably linked to, the second promoter and to the second enhancer;

wherein the first and second transgenes, in the adult form of the nonhuman mammal or the female descendant, express the first and second secretory-recombinant DNA segments in the mammary secretory cells to produce forms of α1(I) and α2(I) procollagen that are processed and secreted by the mammary secretory cells into milk as a trimer comprising at least one chain of α1(I) procollagen or collagen and at least one chain of α2(I) procollagen or collagen.

14. The transgenic nonhuman mammal of claim 1 that is an embryo.

15. The transgenic nonhuman mammal of claim 1, that is a bovine.

16. The transgenic nonhuman mammal of claim 1, that is a mouse.

17. The transgenic nonhuman mammal of claim 1, wherein the trimer is a homotrimer.

18. The transgenic nonhuman mammal of claim 1, further comprising a second transgene comprising:

a second mammary-gland specific promoter, the same or different from the mammary-gland specific promoter;

a second mammary-gland specific enhancer, the same or different from the mammary-gland specific enhancer;

a second DNA segment encoding a second signal sequence capable of targeting the expressing of a polypeptide operably linked to the signal sequence to the endoplasmic reticulum of a cell;

a second recombinant DNA segment encoding a second human procollagen polypeptide operably linked to the second secretory DNA segment to form a second secretory-recombinant DNA segment, said secretory-recombinant DNA segment being operably linked to the second promoter and to the second enhancer, wherein the first and second transgenes, in the adult form of the nonhuman mammal or the female descendant, express the first and second secretory-recombinant DNA segments in the mammary secretory cells to produce forms of procollagen that are processed and secreted by the mammary secretory cells into milk as a detectable amount of a heterotrimer comprising at least one procollagen or collagen chain expressed from each transgene.

19. A method for preparing procollagen or collagen, the method comprising:

providing a transgenic nonhuman mammal having a transgene comprising:

a mammary-gland specific promoter;

a mammary-gland specific enhancer a secretory DNA segment encoding a signal peptide functional in mammary secretory cells of the transgenic nonhuman mammal; and a recombinant DNA segment encoding an exogenous procollagen polypeptide operably linked to the secretory DNA segment to form a secretory-recombinant DNA segment, the secretory-recombinant DNA segment being operably linked to the promoter and to the enhancer;

wherein the transgene, in an adult form of the nonhuman mammal or a female descendant of the nonhuman mammal, expresses the secretory-recombinant DNA segment in the mammary secretory cells to produce a form of the exogenous procollagen polypeptide that is processed and secreted by the mammary secretory cells into milk as exogenous procollagen or collagen in a detectable amount;

supplementing the diet of the transgenic nonhuman mammal or its female descendant with Vitamin c at a level of 50–1000 mg/kg food;

recovering milk from the adult form of the transgenic nonhuman mammal or its female descendant, wherein the milk comprises exogenous procollagen or collagen in a recoverable amount; and purifying procollagen or collagen from the milk.

20. The method of claim 19, further comprising the step of contacting the procollagen with a proteolytic enzyme to convert the procollagen to collagen.

21. Milk from the transgenic nonhuman mammal of claim 1, the milk comprising the exogenous procollagen or collagen polypeptide.

22. The milk of claim 21, wherein the procollagen or collagen is in trimeric form.

23. The milk of claim 22, wherein the concentration of procollagen or collagen is at least 100 µg/ml.

24. A transgene for expressing procollagen or collagen, the transgene comprising:

a casein promoter;

a casein enhancer;

a genomic DNA segment comprising a segment from a signal peptide coding sequence to a 3' flanking region of a procollagen α2(I) gene, operably linked to the promoter and the enhancer.

25. The transgene of claim 24, further comprising a casein 5' untranslated sequence between the promoter and the genomic DNA segment.

26. A stable mammary-gland derived cell line, having a transgene comprising:

a mammary-gland specific promoter;

a mammary-gland specific enhancer;

a secretory DNA segment encoding a signal peptide functional in the cell line; and a recombinant DNA segment encoding an exogenous procollagen polypeptide operably linked to the secretory DNA segment to form a secretory-recombinant DNA segment, the secretory-recombinant DNA segment being operably linked to the promoter and to the enhancer;

wherein the cell line is induced by a lactogenic hormone to express the transgene to produce a form of the exogenous procollagen polypeptide that is processed and secreted by the cell lines as exogenous procollagen or collagen in trimeric form;

provided the recombinant DNA segment comprises a genomic DNA segment from the α1(I) collagen gene and is without nucleotides 1–114 from the first exon of the gene, and/or without a segment from the first intron of the gene.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

TCGAGATCGA TTCTAGACAT G                                    21

(2) INFORMATION FOR SEQ ID NO:2:

(i) SEQUENCE CHARACTERISTICS:
      (A) LENGTH: 56 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

CCATCACCTT GATCATCAAC CCATCGATCT GCTTCTTTCC AGTCTTTCTA GACATG     56

(2) INFORMATION FOR SEQ ID NO:3:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:3:

ATCGATTTGC TTCTTTCCAG TCTTTCTAGA CATG                      34